US012788776B2

(12) United States Patent
Deukmedjian

(10) Patent No.: US 12,788,776 B2
(45) Date of Patent: Nov. 10, 2026

(54) SYSTEMS AND METHODS FOR REPAIRING SPINAL DISC INJURY OR TREATING SPINAL DISC DISEASE

(71) Applicant: Panacea Spine, LLC, Orlando, FL (US)

(72) Inventor: Ara Deukmedjian, Orlando, FL (US)

(73) Assignee: Panacea Spine, LLC, Orlando, FL (US)

(*) Notice: Subject to any disclaimer, the term of this patent is extended or adjusted under 35 U.S.C. 154(b) by 959 days.

(21) Appl. No.: 17/852,139

(22) Filed: Jun. 28, 2022

(65) Prior Publication Data

US 2023/0414656 A1 Dec. 28, 2023

(51) Int. Cl.
*A61K 33/38* (2006.01)
*A61K 9/00* (2006.01)
(Continued)

(52) U.S. Cl.
CPC ............ *A61K 33/38* (2013.01); *A61K 9/0019* (2013.01); *A61K 9/167* (2013.01); *A61M 5/329* (2013.01);
(Continued)

(58) Field of Classification Search
CPC ...... A61K 33/38; A61K 9/0019; A61K 9/167; A61K 9/06; A61K 9/08; A61K 9/0085; A61M 5/329; A61M 13/00; A61M 29/00; A61M 25/0105; A61M 2210/1003; A61M 11/007; A61M 2202/064; A61M 25/06; A61M 25/09; A61M 2205/0205; A61P 19/00; A61B 2017/00261; A61B 17/1671; A61B 17/32002
See application file for complete search history.

(56) References Cited

U.S. PATENT DOCUMENTS 11,839,414 B1 12/2023 Hyman
12,115,076 B2 10/2024 Ginn
(Continued)

FOREIGN PATENT DOCUMENTS

BG 113013 A 4/2021
EP 2990034 A1 3/2016
(Continued)

OTHER PUBLICATIONS

U.S. Appl. No. 17/964,787, filed Oct. 12, 2022, Systems and Methods for Repairing Spinal Disc Injury or Treating Spinal Disc Disease Using Copper.
(Continued)

*Primary Examiner* — Bhisma Mehta
*Assistant Examiner* — Fatimata Sahra Diop
(74) *Attorney, Agent, or Firm* — Gordon & Jacobson, P.C.

(57) ABSTRACT

A method for treating or repairing a damaged spinal disc of a patient may include inserting, using medical imaging, a shaft with a lumen extending from an exterior of a patient to the damaged spinal disc, dispensing silver particles, using the lumen, to the damaged spinal disc, and removing the hollow shaft from the patient. A system may include a syringe and silver particles in the syringe. A kit may include silver particles, and at least one of a guidewire, one or more dilators, a tubular retractor, a disposable endoscope, a disposable laser fiber; an endoscopic rongeurs, indigo carmine dye, or a fluid adaptor.

22 Claims, 11 Drawing Sheets

SYRINGE PRE-FILLED WITH SILVER PARTICLES (E.G., NANOPARTICLES OR MICROPARTICLES)

(51) Int. Cl.

| | |
|---|---|
| ***A61K 9/16*** | (2006.01) |
| ***A61M 5/32*** | (2006.01) |
| ***A61M 13/00*** | (2006.01) |
| ***A61M 29/00*** | (2006.01) |
| *A61M 25/01* | (2006.01) |

(52) U.S. Cl.

CPC ............ *A61M 13/00* (2013.01); *A61M 29/00* (2013.01); *A61M 25/0105* (2013.01); *A61M 2210/1003* (2013.01)

(56) References Cited

U.S. PATENT DOCUMENTS

| | | | | |
|---|---|---|---|---|
| 2003/0083642 | A1* | 5/2003 | Boyd | A61B 17/8811 604/164.11 |
| 2003/0229353 | A1* | 12/2003 | Cragg | A61B 17/1757 606/86 R |
| 2007/0027230 | A1 | 2/2007 | Beyar | |
| 2007/0081958 | A1 | 4/2007 | Bechert et al. | |
| 2007/0213824 | A1* | 9/2007 | Trieu | A61B 17/7061 623/17.11 |
| 2008/0086133 | A1 | 4/2008 | Kuslich | |
| 2008/0221628 | A1* | 9/2008 | Milbocker | A61B 17/0057 604/509 |
| 2008/0262583 | A1* | 10/2008 | Sharkey | A61B 18/1482 606/190 |
| 2009/0105366 | A1 | 4/2009 | Vogt | |
| 2009/0149954 | A1 | 6/2009 | Hu | |
| 2012/0116515 | A1 | 5/2012 | Semler | |
| 2012/0128777 | A1 | 5/2012 | Keck et al. | |
| 2012/0244224 | A1 | 9/2012 | Biris et al. | |
| 2013/0317296 | A1* | 11/2013 | To | A61B 17/1671 600/114 |
| 2014/0037742 | A1 | 2/2014 | Fagan | |
| 2015/0290354 | A1* | 10/2015 | Loboa | A61L 15/26 424/618 |
| 2016/0114112 | A1* | 4/2016 | Riebman | A61B 17/00491 604/500 |
| 2017/0100338 | A1 | 4/2017 | Awad et al. | |
| 2019/0094679 | A1* | 3/2019 | Shukla | C08L 1/12 |
| 2020/0095421 | A1 | 3/2020 | Kettel | |
| 2020/0108093 | A1 | 4/2020 | Simeroth | |
| 2021/0030789 | A1* | 2/2021 | Lau | A61K 38/50 |
| 2021/0038772 | A1 | 2/2021 | Faucher et al. | |
| 2021/0282937 | A1* | 9/2021 | Seifert | A61F 2/4611 |
| 2021/0322634 | A1 | 10/2021 | Zheng | |
| 2022/0062174 | A1 | 3/2022 | Greenhalgh | |
| 2022/0105316 | A1* | 4/2022 | Lutz | A61M 25/0102 |
| 2022/0296378 | A1 | 9/2022 | Ginn | |
| 2022/0304814 | A1 | 9/2022 | Ginn | |

FOREIGN PATENT DOCUMENTS

| | | | |
|---|---|---|---|
| EP | 3567114 | A1 | 11/2019 |
| WO | WO-2014147638 | A1 | 9/2014 |
| WO | WO-2018015976 | A1 | 1/2018 |

OTHER PUBLICATIONS

Deukmedjian, Ara, et al., "Cervical Deuk Laser Disc Repair® A novel, full-endoscopic surgical technique for the treatment of symptomatic cervical disc disease", Surgical Neurology International, 3:142, [Online]. Retrieved from the Internet: <URL: http://www.surgicalneurologyint.com/text.asp?2012/3/1/142/103884>, (2012), 6 pgs.

Deukmedjian, Ara, et al., "Deuk Laser Disc Repair® is a safe and effective treatment for symptomatic cervical disc disease", Surgical Neurology International, 4:68, [Online]. Retrieved from the Internet: <URL: http://www.surgicalneurologyint.com/text.asp?2013/4/1/68/112610>, (2013), 7 pgs.

Marassi, Valentina, et al., "Silver nanoparticles as a medical device in healthcare settings: a five-step approach for candidate screening of coating agents", Royal Society Open Science, 5: 171113., [Online]. Retrieved from the Internet: <URL: http://dx.doi.org/10.1098/rsos.171113>, (2018), 21 pgs.

Non Final Office Action U.S. Appl. No. 17/964,787, dated Oct. 16, 2025.

* cited by examiner

SYRINGE PRE-FILLED WITH SILVER PARTICLES (E.G., NANOPARTICLES OR MICROPARTICLES)

VIAL OF SILVER PARTICLES (E.G., NANOPARTICLES OR MICROPARTICLES) FOR DRAWING INTO SYRINGE

SYSTEMS AND METHODS FOR REPAIRING SPINAL DISC INJURY OR TREATING SPINAL DISC DISEASE

TECHNICAL FIELD

This document relates generally to medical systems, and more particularly, but not by way of limitation, to systems, devices, and methods for treating or repairing spinal discs, such as spinal discs that may be damaged from spinal disc disease or injured.

BACKGROUND

The spinal column includes 24 vertebrae, including seven cervical vertebrae (C1-C7) corresponding the neck, twelve thoracic vertebrae (T1-T12) corresponding to the middle of the back, and five lumbar vertebrae (L1-L5) corresponding to the lower back. The spinal column protects the spinal cord. Nerve roots branch off from the spinal cord and pass through foramen (or foramin) of vertebrae. The vertebrae are separated by spinal discs, which may also be referred to as intervertebral discs. Each disc includes an annulus fibrosus (or simply referred to as the annulus) that surrounds a gel-like substance referred to a nucleus pulposus (or simply referred to as the nucleus).

Spinal discs may be abnormal, damaged or injured. The term "damaged disc" is intended to include abnormal discs or injured discs. A disc may be damaged because of degeneration or disc disease, or may be damaged because of trauma. Both disc trauma or disc disease may cause the annulus to tear. By way of example and not limitation, a damaged disc may include a partial or full tear in the annulus. A disc herniation occurs when the nucleus pushes through an annular tear.

What is needed is an improved treatment of damaged spinal discs.

SUMMARY

An example (e.g., "Example 1") may include a method for treating or repairing a damaged spinal disc of a patient. The method may include inserting, using medical imaging, a shaft with a lumen extending from an exterior of a patient to the damaged spinal disc, dispensing silver particles, using the lumen, to the damaged spinal disc, and removing the hollow shaft from the patient.

In Example 2, the subject matter of Example 1 may optionally be configured such that the hollow shaft is within a range from 1 mm to 12 mm in diameter.

In Example 3, the subject matter of Example 2 may optionally be configured such that inserting the shaft includes inserting a hypodermic needle, using the medical imaging, to the damaged spinal disc.

In Example 4, the subject matter of Example 2 may optionally be configured such that the shaft is an endoscopic tubular retractor, and to further include inserting a guidewire, using a guidewire introducer needle and the medical imaging, to the damaged spinal disc, inserting at least one hollow dilator over the guidewire to the damaged spinal disc, inserting the endoscopic tubular retractor over the at least one hollow dilator to the damaged spinal disc, and removing the guidewire and the at least one hollow dilator from the endoscopic tubular retractor, wherein the endoscopic tubular retractor includes the lumen used to dispense silver particles to the annular tear.

In Example 5, the subject matter of Example 4 may optionally be configured to further include using a tool inserted into the endoscopic tubular retractor to dispense the silver particles to the damaged spinal disc.

In Example 6, the subject matter of Example 5 may optionally be configured to further include a syringe with a barrel containing the silver particles, a plunger, and a needle advanced into the lumen of the endoscopic tubular retractor to dispense the silver particles to the damaged spinal disc by actuating the plunger to push the silver particles through the needle.

In Example 7, the subject matter of Example 6 may optionally be configured such that the needle may include a hypodermic needle or a flexible dispensing needle.

In Example 8, the subject matter of any one or more of Examples 5-7 may optionally be configured to further include using a steerable catheter to dispense the silver particles to the damaged spinal disc, including feeding a distal end of the steerable catheter through the lumen of the endoscopic tubular retractor and steering the distal end to dispense the silver particles through a lumen in the steerable catheter to the damaged spinal disc.

In Example 9, the subject matter of Example 8 may optionally be configured to further include introducing the silver particles into the lumen in the steerable catheter, using gravity to dispense the silver particles to the damaged spinal disc.

In Example 10, the subject matter of Example 9 may optionally be configured to further include using an endoscopic camera to visualize a distribution of the silver particles on a surface of the damaged spinal disc.

In Example 11, the subject matter of any one or more of Examples 5-10 may optionally be configured to further include using the tool inserted into the endoscopic tubular retractor to atomize the silver particles into an aerosol or small droplets into a gas phase to coat a surface region of the damaged spinal disc.

In Example 12, the subject matter of Example 11 may optionally be configured to further include using sterile compressed air to atomize the silver particles to coat the surface region, the sterile compressed air being appropriately sterile for introduction into a surgical field.

In Example 13, the subject matter of any one or more of Examples 11-12 may optionally be configured to further include using air in a syringe to atomize the silver particles to coat the surface region of the damaged spinal disc.

In Example 14, the subject matter of any one or more of Examples 1-13 may optionally be configured such that inserting the shaft using medical imaging includes using at least one of X-ray guided imaging (e.g., CT scans or fluoroscopy), stereotactic techniques, or robotic navigation to insert the shaft.

In Example 15, the subject matter of any one or more of Examples 1-14 may optionally be configured to further include using the medical imaging to advance the hollow shaft through a foramen in a spine to access the damaged spinal disc.

In Example 16, the subject matter of any one or more of Examples 1-14 may optionally be configured to further include advancing the hollow shaft to enter an anterior side of the damaged spinal disc to a damaged on a posterior side of the damaged spinal disc.

In Example 17, the subject matter of any one or more of Examples 1-16 may optionally be configured such that the silver particles are provided in a dry powder.

In Example 18, the subject matter of any one or more of Examples 1-16 may optionally be configured such that the silver particles are provided in a liquid solution.

In Example 19, the subject matter of Example 18 may optionally be configured such that the liquid solution includes saline or a Lactated Ringer's solution.

In Example 20, the subject matter of any one or more of Examples 1-16 may optionally be configured such that the silver particles are provided in a gel suspension.

In Example 21, the subject matter of any one or more of Examples 1-20 may optionally be configured such that the silver particles have dimensions within a range between 1 nm and 1000 nm.

In Example 22, the subject matter of any one or more of Examples 1-21 may optionally be configured such that the silver particles are coated with hydroxyethyl cellulose.

In Example 23, the subject matter of any one or more of Examples 1-22 may optionally be configured to further include endoscopically debriding the damaged spinal disc before distributing the silver particles.

In Example 24, the subject matter of Example 23 may optionally be configured to include using a medical laser or radio frequency (RF) probe to endoscopically debride the damaged spinal disc before dispensing the silver particles to the damaged spinal disc.

In Example 25, the subject matter of any one or more of Examples 23-24 may optionally be configured to remove nucleus pulposus that pushed through an annular tear.

An example (e.g., "Example 26") may include a method for treating or repairing a damaged spinal disc of a patient. The method may include inserting a guidewire, using medical imaging, from an exterior of the patient to the annular tear of the spinal disc, inserting a hollow dilator over the guidewire to the damaged spinal disc, inserting an endoscopic tubular retractor over the dilator from the exterior of the patient to the damaged spinal disc, removing the guidewire and the hollow dilator from the endoscopic tubular retractor, inserting a laser or radio frequency (RF) probe into the endoscopic tubular retractor, irrigating a surgical field near the damaged spinal disc, and using the laser or the RF probe to debride the damaged spinal disc, after debriding the damaged spinal disc, dispensing silver particles to the damaged spinal disc via the endoscopic tubular retractor, and removing the endoscopic tubular retractor from the patient.

In Example 27, the subject matter of Example 26 may optionally be configured such that inserting the guidewire using the medical imaging includes using at least one of X-ray guided imaging (e.g., CT scans or fluoroscopy), stereotactic techniques, or robotic navigation to insert the guidewire.

In Example 28, the subject matter of any one or more of Examples 26-27 may optionally be configured to further include using the medical imaging to advance the hollow shaft through a foramen in a spine to access the damaged spinal disc.

In Example 29, the subject matter of any one or more of Examples 26-27 may optionally be configured to further include advancing the hollow shaft to enter an anterior side of the damaged spinal disc to a damaged region on a posterior side of the damaged spinal disc.

In Example 30, the subject matter of any one or more of Examples 26-29 may optionally be configured such that the silver nanoparticles are provided in a dry powder.

In Example 31, the subject matter of any one or more of Examples 26-29 may optionally be configured such that the silver nanoparticles are provided in a liquid solution.

In Example 32, the subject matter of Example 31 may optionally be configured such that the liquid solution includes saline or a Lactated Ringer's solution.

In Example 33, the subject matter of any one or more of Examples 26-29 may optionally be configured such that the silver nanoparticles are provided in a gel suspension.

In Example 34, the subject matter of any one or more of Examples 26-33 may optionally be configured such that the silver particles have dimensions within a range between 1 nm and 1000 nm.

In Example 35, the subject matter of any one or more of Examples 26-34 may optionally be configured such that the silver particles are coated with hydroxyethyl cellulose.

In Example 36, the subject matter of any one or more of Examples 26-35 may optionally be configured to further include using an endoscopic camera to visualize a distribution of the silver particles on a surface of the damaged spinal disc.

In Example 37, the subject matter of Example 36 may optionally be configured such that the distribution of the silver particles includes a color additive to enhance visualization using the endoscopic camera.

An example (e.g., "Example 38") may include a method for treating or repairing a damaged spinal disc of a patient using a syringe with a barrel a syringe with a barrel containing the silver particles, a plunger, and a hypodermic needle. The method may include inserting the hypodermic needle of the syringe, using medical imaging, into the patient to the damaged spinal disc, actuating the plunger to push the silver particles out of the barrel through the hypodermic needle to distribute the silver particles to the damaged spinal disc, and removing the hypodermic needle of the syringe from the patient.

In Example 39, the subject matter of Example 38 may optionally be configured such that inserting the hypodermic needle using the medical imaging includes using at least one of X-ray guided imaging, stereotactic techniques, or robotic navigation to insert the hypodermic needle.

In Example 40, the subject matter of any one or more of Examples 38-39 may optionally be configured to further include using the medical imaging to advance the hollow shaft through a foramen in a spine to access the damaged spinal disc.

In Example 41, the subject matter of any one or more of Examples 38-39 may optionally be configured to further include advancing the hollow shaft to enter an anterior side of the damaged spinal disc to enter a damaged region on a posterior side of the damaged spinal disc.

In Example 42, the subject matter of any one or more of Examples 38-39 may optionally be configured such that the silver particles are provided in a dry powder.

In Example 43, the subject matter of any one or more of Examples 38-39 may optionally be configured such that the silver particles are provided in a liquid solution.

In Example 44, the subject matter of Example 43 may optionally be configured such that the liquid solution includes saline or a Lactated Ringer's solution.

In Example 45, the subject matter of any one or more of Examples 38-39 may optionally be configured such that the silver particles are provided in a gel suspension.

In Example 46, the subject matter of any one or more of Examples 38-45 may optionally be configured such that the silver particles have dimensions within a range between 1 nm and 1000 nm.

In Example 47, the subject matter of any one or more of Examples 38-46 may optionally be configured such that the silver particles are coated with hydroxyethyl cellulose.

An example (e.g., "Example 48") of a system may be configured for use in treating or repairing a damaged spinal disc. The system may include a syringe, and silver particles in the syringe. The syringe may include a barrel with the silver particles therein, a plunger and a needle, where the syringe is configured to distribute the silver particles through the needle when the plunger is pushed into the barrel.

In Example 49, the subject matter of Example 48 may optionally be configured such that the needle includes a hypodermic needle configured to be inserted to a damaged spinal disc to dispense the silver particles to the damaged spinal disc.

In Example 50, the subject matter of Example 48 may optionally be configured such that the needle includes a spinal needle configured to reach tissue near a spine.

In Example 51, the subject matter of any one or more of Examples 48-50 may optionally be configured such that the silver particles in the syringe are a dry powder.

In Example 52, the subject matter of any one or more of Examples 48-50 may optionally be configured such that the silver particles in the syringe are in a liquid solution.

In Example 53, the subject matter of Example 52 may optionally be configured such that the liquid solution includes saline or a Lactated Ringer's solution.

In Example 54, the subject matter of any one or more of Examples 48-50 may optionally be configured such that the silver particles in the syringe are in a gel suspension.

In Example 55, the subject matter of any one or more of Examples 48-54 may optionally be configured such that the silver particles have dimensions within a range between 1 nm and 1000 nm.

In Example 56, the subject matter of any one or more of Examples 48-55 may optionally be configured such that the silver particles are coated with hydroxyethyl cellulose.

An example (e.g., "Example 57") of a system may be a kit configured for use in treating or repairing a damaged spinal disc. The kit may include silver particles, and at least one of a guidewire, one or more dilators; a tubular retractor, a disposable endoscope, a disposable laser fiber; an endoscopic rongeurs, indigo carmine dye, or a fluid adaptor.

In Example 58, the subject matter of Example 57 may optionally be configured such that the silver particles are in a dry powder.

In Example 59, the subject matter of Example 57 may optionally be configured such that the silver particles are in a liquid solution.

In Example 60, the subject matter of Example 59 may optionally be configured such that the silver particles are in saline or a Lactated Ringer's solution.

In Example 61, the subject matter of Example 57 may optionally be configured such that the silver particles are in a gel suspension.

In Example 62, the subject matter of any one or more of Examples 57-61 may optionally be configured such that the silver particles have dimensions within a range between 1 nm and 1000 nm.

In Example 63, the subject matter of any one or more of Examples 57-62 may optionally be configured such that the silver particles are coated with hydroxyethyl cellulose.

In Example 64, the subject matter of any one or more of Examples 57-63 may optionally be configured such that a dyed material is included with the silver particles for enhancing visualization using an endoscopic camera.

In Example 65, the subject matter of any one or more of Examples 57-64 may optionally be configured such that the silver particles include at least two ranges of silver particle ranges, where a first range includes larger particles and a second range includes smaller particles, the larger particles in the first range is less than 50 wt-% of total weight of the silver particles.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
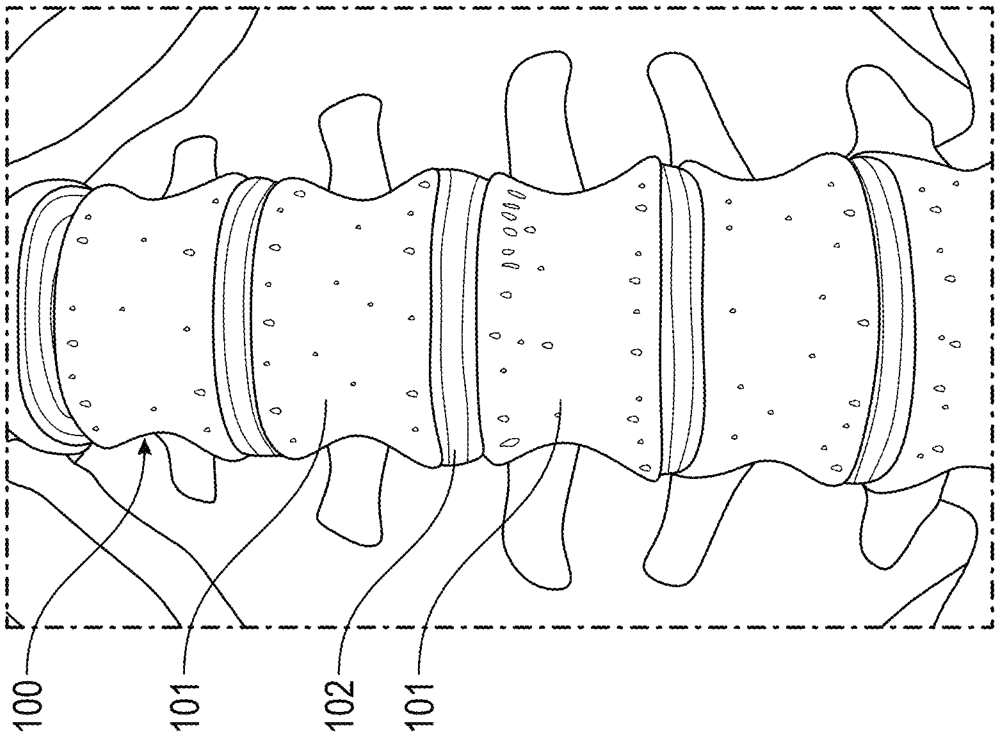
FIG. 1 illustrates a portion of the spinal column.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The spinal column includes 24 vertebrae, including the cervical vertebrae (C1-C7) corresponding the neck, the thoracic vertebrae (T1-T12) corresponding to the middle of the back, and lumbar vertebrae (L1-L5) corresponding to the lower back. The spinal column protects the spinal cord and nerve roots that branch off from the spinal cord and pass through foramen of vertebrae. The vertebrae are separated by spinal discs, which may also be referred to as intervertebral discs. Each disc includes an annulus fibrous (or simply referred to as the annulus) that surrounds a gel-like substance referred to a nucleus pulposus (or simply referred to as the nucleus). The term "spinal disc" includes spinal discs in the cervical region, spinal discs in the thoracic region and spinal discs in the lumbar region.

A disc may be damaged because of degeneration or disc disease, or because of trauma. A damaged spinal disc may include, but is not limited to, a herniated disc, a bulging disc, disc bulge, a ruptured disc, a degenerated disc, a desiccated disc or disc desiccation, a protruding disc, an annular tear, an extruded disc, a degenerative disc disease, a disc osteophyte complex, a spondylosis, and a disc protrusion. For example, the annulus may tear because of trauma or degeneration. By way of example and not limitation, a damaged disc may include a partial or full tear in the annulus. A disc herniation occurs when the nucleus pushes through an annular tear.

Disc herniations are a common cause of pain. For example, an inflamed annular tear corresponding to a disc herniation in the cervical region can cause neck pain and a disc herniation in the lumbar region can cause back pain. The disc herniation may inflame the nerve roots, which may cause arm pain for cervical disc herniation and can cause leg pain for lumbar disc herniation. The annular tear may take up to 12 months to heal on its own.

However, the present subject matter is not limited to treating disc herniations. Various embodiments disclosed herein treat or repair damaged discs that may result from various causes. For example, treated conditions may include spinal disc injury: spinal stenosis, neural foraminal narrowing, neural foraminal stenosis, neural foraminal encroachment, neural foraminal compromise, nerve root impingement, spondylolisthesis, degenerative scoliosis, facet joint disease, and facet joint arthropathy. According to various embodiments, silver particles (e.g., nanoparticles and/or microparticles) may be distributed to the abnormal or damaged disc when the damaged disc is accompanied by symptoms such as pain. The pain may be, but is not limited to, back pain, neck pain or thoracic pain. The silver particles may be distributed to the abnormal or damaged disc when the damaged disc in not accompanied by symptoms.

Figure 2:
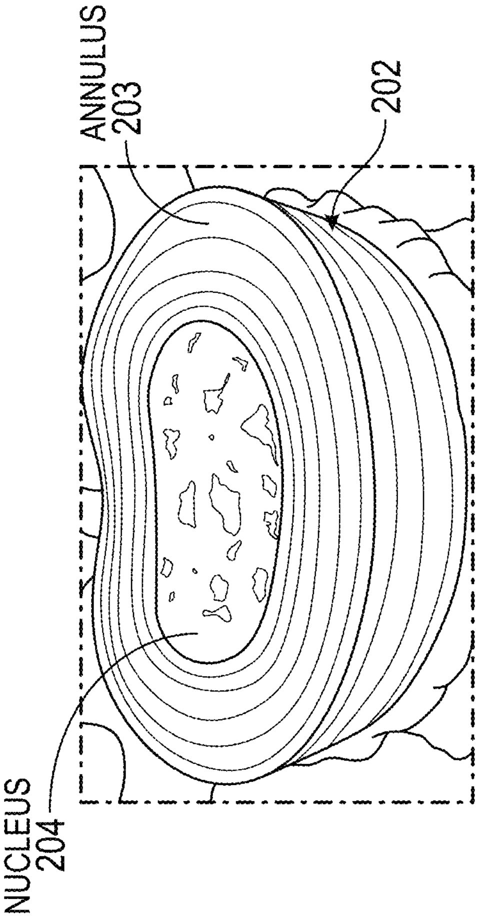
FIG. 2 illustrates a spinal disc in the spinal column.
Figure 3:
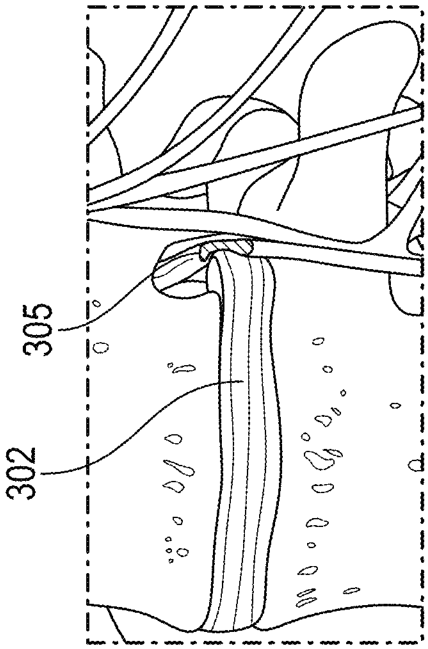
FIG. 3 illustrates a disc herniation pressing against and inflaming nerve roots.

FIG. 1 illustrates a portion of the spinal column 100 including vertebrae 101 separated from each other by spinal discs 102 (intervertebral discs). FIG. 2 illustrates a spinal disc 202 in the spinal column. The illustrated spinal disc 202 includes an annulus fibrosus 203 ("annulus") that surrounds the gel-like nucleus pulposus 204 ("nucleus"). FIG. 3 illustrates a herniated disc 302 pressing against and inflaming nerve roots 305. Again, a disc herniation is one example of a damaged disc.

Figure 4:
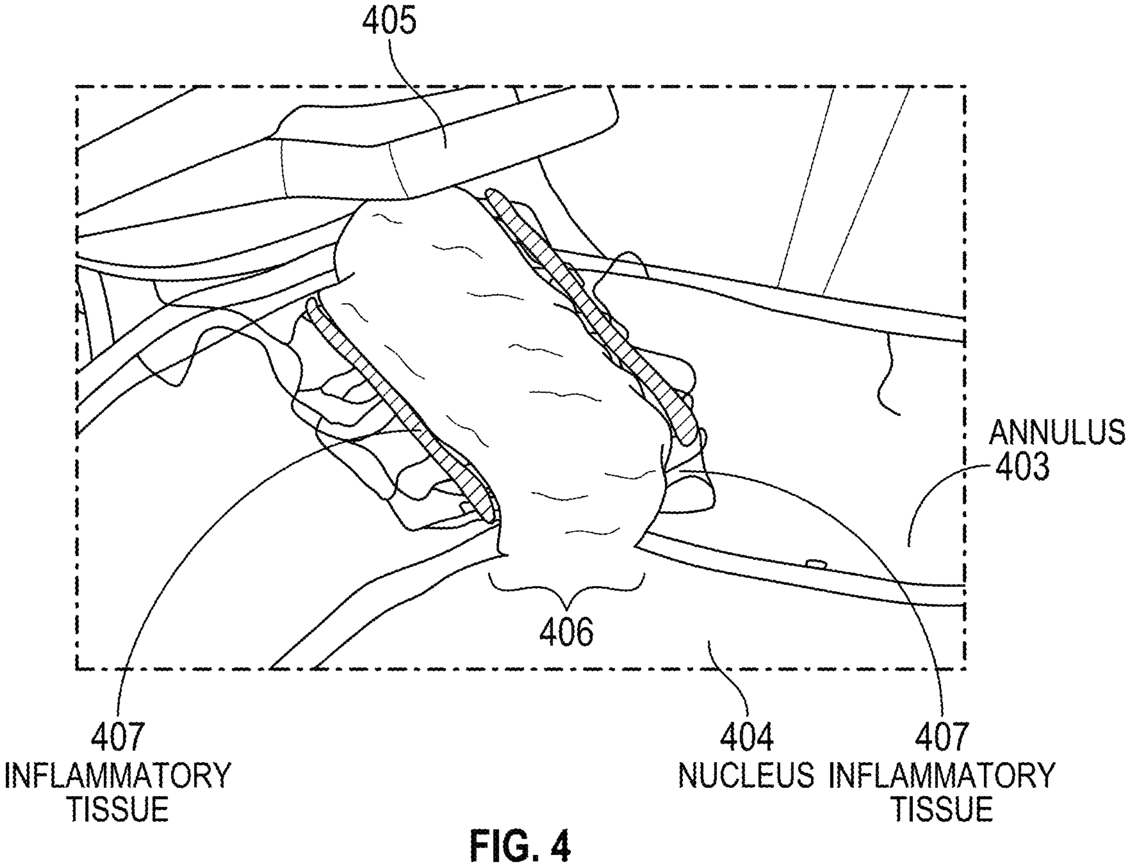
FIG. 4 illustrates a damaged disc that includes a disc herniation and an inflamed annular tear.

FIG. 4 illustrates a damaged disc that includes a disc herniation and an inflamed annular tear. The figure illustrates the annulus 403, the nucleus 404, and nerve roots 405. There is a tear 406 in the annulus. The tear 406 may have been caused by a traumatic injury or degeneration. Pressure on the disc causes herniation of the nucleus 404 through the tear 406. Inflammatory tissue 407 develops within the annular tear causing pain signals. For example, the pain may be experienced as leg pain for herniated discs in the lumbar region or neck pain for herniated discs in the cervical region. Inflammation from the annular tear can spread to nearby nerve roots, which also causes pain. The nucleus contact with the tear can cause an inflammatory cascade which can cause the tissue to dry out, fragment and fray. It is believed that "discogenic pain" originates from sensitized nascent nerve fibers located in the posterior annulus surrounding symptomatic annular tears; and these nerve fibers originate from branches of the sinuvertebral nerve and their growth into the posterior annulus is most likely induced by inflammatory cytokines concentrated around the symptomatic annular tear. Deukmedjian A J, Jason Cutright S T, Cianciabella P C A, Deukrnedjian A Deuk Laser Disc Repair® is a safe and effective treatment for symptomatic cervical disc disease. Surg Neurol Int 2013; 4:68. The present subject matter may be used to treat the spinal disc throughout the continuum of damage, including damage that occurs before a tear forms or progresses to a complete form.

Various embodiments of the present subject matter described herein use silver particles (e.g., nanoparticles and/or microparticles) to treat a damaged disc, such as but not limited to an annular tear. As used herein, the term silver particles is intended to include only silver nanoparticles, only silver microparticles, or both silver nanoparticles and silver microparticles. Microparticles have sizes greater than or equal to 1 μm (e.g., within a range greater or equal to 1 μm to 1,000 μm or various subranges therein, and nanoparticles have sizes less than 1 μm or 1,000 nm (e.g., within a range of 1 nm to 1,000 nm or various subranges therein). It is believed that the silver particles will speed up the healing of the damaged spinal disc, which is desirable to treat annular tears as annular tears may take up to twelve months to heal on its own. The silver particles may be dispensed to the damaged disc using a minimally invasive technique such as an injection through a needle or an endoscopic surgical process. Various embodiments further debride the inflamed tissue before dispensing the silver particles to the damaged disc. For example, a laser or radio frequency (RF) probe may access the annular tear through an endoscopic surgical process, and may be used to debride the annular tear. Examples of a laser include Holmium: YAG (Ytrium Argon, Garnet) laser or a $CO_2$ lasers. The laser or RF probe effectively vaporizes the targeted tissue. For example, the laser may be used to remove the herniated nucleus as well as the nucleus and inflamed tissue within the annular tear.

By way of example and not limitation, the present subject matter may, according to various embodiments, coat the silver particles with hydroxyethyl cellulose. Various embodiments may provide the silver particles in a dry power. Various embodiments may provide the silver particles in a gel suspension. Various embodiments may provide the silver particles in a liquid solution such as a saline or a Lactated Ringer's solution. Saline is composed of water and 0.9% sodium chloride. Lactated Ringer's is a sterile solution composed of water, sodium chloride (salt), sodium lactate, potassium chloride, and calcium chloride, and it may be substituted for saline solution (water and 0.9% sodium chloride). These solutions have an appropriate amount of ions and may be used for irrigation. A color additive (e.g., dye) may be included (e.g., into solution, a suspension or carrier) to enhance visualization of the distributed silver particles using an endoscopic camera.

Various embodiments may deliver a silver particle containing composition. Compositions comprising silver particles may conveniently be provided in the form of formulations suitable for administration. A suitable administration format may best be determined by a medical practitioner for each patient individually, according to standard procedures. Suitable pharmaceutically acceptable carriers (excipients) and their formulation are described in standard formulations treatises, e.g., Remington's Pharmaceuticals Sciences. By "pharmaceutically acceptable" it is meant a carrier, diluent, excipient, and/or salt that is compatible with the other ingredients of the formulation, and not deleterious to the recipient thereof.

Compositions may be formulated in solution at neutral pH, for example, about pH 6.5 to about pH 8.5, or from about pH 7 to 8, with an excipient to bring the solution to about isotonicity, for example, 4.5% mannitol or 0.9% sodium chloride, pH buffered with art-known buffer solutions, such as sodium phosphate, that are generally regarded as safe, together with an accepted preservative such as metacresol 0.1% to 0.75%, or from 0.15% to 0.4% metacresol. Obtaining a desired isotonicity can be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is useful for buffers containing sodium ions. If desired, solutions of the above compositions can also be prepared to enhance shelf life and stability. Therapeutically useful compositions can be prepared by mixing the ingredients following generally accepted procedures. For example, the selected components can be mixed to produce a concentrated mixture which may then be adjusted to the final concentration and viscosity by the addition of water and/or a buffer to control pH or an additional solute to control tonicity.

The silver particle containing composition may be liquid, e.g., aqueous, or a gel, e.g., a hydrogel. For example, the silver particles may be in a material including but not limited to hydrogels of poloxamers, polyacrylamide, poly(2-hydroxyethyl methacrylate), carboxyvinyl-polymers (e.g., Carbopol 934, Goodrich Chemical Co.), cellulose derivatives, e.g., methylcellulose, cellulose acetate, hydroxyethyl cellulose and hydroxypropyl cellulose, polyvinyl pyrrolidone or polyvinyl alcohols, or combinations thereof.

In some embodiments, the silver particles are in a biocompatible material such as a polymeric material derived from a biodegradable polymeric such as collagen, e.g., hydroxylated collagen, fibrin, polylactic-polyglycolic acid, or a polyanhydride. Other examples include, without limitation, any biocompatible polymer, whether hydrophilic, hydrophobic, or amphiphilic, such as ethylene vinyl acetate copolymer (EVA), polymethyl methacrylate, polyamides, polycarbonates, polyesters, polyethylene, polypropylenes, polystyrenes, polyvinyl chloride, polytetrafluoroethylene, N-isopropylacrylamide copolymers, poly(ethylene oxide)/poly(propylene oxide) block copolymers, poly(ethylene glycol)/poly(D,L-lactide-co-glycolide) block copolymers, polyglycolide, polylactides (PLLA or PDLA), poly(caprolactone) (PCL), or poly(dioxanone) (PPS).

In another embodiment, the biocompatible material includes polyethyleneterephalate, polytetrafluoroethylene, copolymer of polyethylene oxide and polypropylene oxide, a combination of polyglycolic acid and polyhydroxyalkanoate, gelatin, alginate, poly-3-hydroxybutyrate, poly-4-hydroxybutyrate, and polyhydroxyoctanoate, and polyacrylonitrilepolyvinylchlorides.

In one embodiment, the following polymers may be employed, e.g., natural polymers such as starch, chitin, glycosaminoglycans, e.g., hyaluronic acid, dermatan sulfate and chrondrotin sulfate, and microbial polyesters, e.g., hydroxyalkanoates such as hydroxyvalerate and hydroxybutyrate copolymers, and synthetic polymers, e.g., poly (orthoesters) and polyanhydrides, and including homo and copolymers of glycolide and lactides (e.g., poly(L-lactide, poly(L-lactide-co-D,L-lactide), poly(L-lactide-co-glycolide, polyglycolide and poly(D,L-lactide), pol(D,L-lactide-coglycolide), poly(lactic acid colysine) and polycaprolactone.

In one embodiment, the biocompatible material is derived from isolated extracellular matrix (ECM). ECM may be isolated from endothelial layers of various cell populations, tissues and/or organs, e.g., any organ or tissue source including the dermis of the skin, liver, alimentary, respiratory, intestinal, urinary or genital tracks of a warm blooded vertebrate. ECM employed in the invention may be from a combination of sources. Isolated ECM may be prepared in particulate form, gel form and the like.

The biocompatible scaffold polymer may comprise silk, elastin, chitin, chitosan, poly(d-hydroxy acid), poly(anhydrides), or poly(orthoesters). More particularly, the biocompatible polymer may be formed of polyethylene glycol, poly(lactic acid), poly(glycolic acid), copolymers of lactic and glycolic acid, copolymers of lactic and glycolic acid with polyethylene glycol, poly(E-caprolactone), poly(3-hydroxybutyrate), poly(p-dioxanone), polypropylene fumarate, poly(orthoesters), polyol/diketene acetals addition polymers, poly(sebacic anhydride) (PSA), poly(carboxybis-carboxyphenoxyphenoxy hexone (PCPP) poly[bis (p-carboxypheonoxy) methane] (PCPM), copolymers of SA, CPP and CPM, poly(amino acids), poly(pseudo amino acids), polyphosphazenes, derivatives of poly[(dichloro)phosphazenes] or poly[(organo) phosphazenes], poly-hydroxybutyric acid, or S-caproic acid, polylactide-co-glycolide, polylactic acid, polyethylene glycol, cellulose, oxidized cellulose, alginate, gelatin or derivatives thereof.

Thus, the polymer may be formed of any of a wide range of materials including polymers, including naturally occurring polymers, synthetic polymers, or a combination thereof. In one embodiment, the polymer includes but is not limited to alginate, chitosan, poly(2-hydroxyethylmethacrylate), xyloglucan, co-polymers of 2-methacryloyloxyethyl phosphorylcholine, poly(vinyl alcohol), silicone, hydrophobic polyesters and hydrophilic polyester, poly(lactide-co-glycolide), N-isoproylacrylamide copolymers, poly(ethylene oxide)/poly(propylene oxide), polylactic acid, poly(orthoesters), polyanhydrides, polyurethanes, copolymers of 2-hydroxyethylmethacrylate and sodium methacrylate, phosphorylcholine, cyclodextrins, polysulfone and polyvinylpyrrolidine, starch, poly-D,L-lactic acid-para-dioxanone-polyethylene glycol block copolymer, polypropylene, poly(ethylene terephthalate), poly(tetrafluoroethylene), poly-epsilon-caprolactone, or crosslinked chitosan hydrogels.

The amount of a composition(s) administered to achieve a particular outcome will vary depending on various factors including, but not limited to, the formulation, the condition, patient specific parameters, e.g., height, weight and age, and whether prevention or treatment, is to be achieved.

In one embodiment, the amount of silver particles in a composition to be administered may be about 90, 80, 70, 60, 50, 40, 30, 20, 10, 5, or 1 wt %. In one embodiment, the amount of silver particles in a composition to be administered may be about 0.5, 0.1, 0.05, 0.01, 0.005, or 0.001 wt %. In one embodiment, the silver particles are about 5 nm to 10 nm, about 10 nm to 20 nm, about 5 μm to 10 μm or about 10 μm to 20 μm average diameter.

In one embodiment, the amount of silver particles in a composition to be administered may be about 5, 10, 20, 30, 40, 50, 60, 70, 80, 90, or 100 μg/mL. In one embodiment, the amount of silver particles in a composition to be administered may be about 5, 10, 20, 30, 40, 50, 60, 70, 80, 90, or 100 ng/mL. In one embodiment, the amount of silver particles in a composition to be administered may be about 5, 10, 20, 30, 40, 50, 60, 70, 80, 90, or 100 mg/mL. In one embodiment, the silver particles are about 5 nm to 10 nm, about 10 nm to 20 nm, about 5 μm to 10 μm or about 10 μm to 20 μm average diameter.

The surface of the silver particles may be modified, e.g., to increase retention time at the site of administration, increase biocompatibility, e.g., decrease toxicity, or otherwise increase ease of administration. The surface may be modified with a targeting molecule, a protein, e.g., an antibody or a fragment thereof, albumin, such as human serum albumin, or other ligand, a lipid, e.g., phospholipids, a glycolipid, glycoprotein, a polymer such as PEG, PEI, PLA, PGLA, hydroxyethyl cellulose, hydroxymethyl cellulose, phosphorylcholine, or phosphorylethanolamine The compositions can be provided in a dosage form containing an amount effective in one or multiple doses. For example, the active agent may be administered in dosages of at least about 0.0001 mg/kg to about 1 mg/kg, of at least about 0.001 mg/kg to about 0.5 mg/kg, at least about 0.01 mg/kg to about 0.25 mg/kg or at least about 0.01 mg/kg to about 0.25 mg/kg of body weight, although other dosages may provide beneficial results. In one embodiment, the silver particles are about 5 nm to 10 nm, about 10 nm to 20 nm, about 5 μm to 10 μm or about 10 μm to 20 μm average diameter. The amount administered will vary depending on various factors including, but not limited to, the agent and/or carrier chosen for administration, the disease, the weight, the physical condition, the health, and/or the age of the mammal. Such factors can be readily determined by the clinician employing animal models or other test systems that are available in the art. As noted, the exact dose to be administered is determined by the attending clinician but may be in 0.5 mL, 1 mL, 1.5 mL or 2.0 mL phosphate buffered saline.

For example, the composition/active agent(s) can be administered in dosages of at least about 0.0001 mg/kg to about 1 mg/kg, of at least about 0.01 mg/kg to about 5.0 mg/kg, at least about 0.1 mg/kg to about 2.5 mg/kg or at least about 1 mg/kg to about 5 mg/kg of body weight, although other dosages may provide beneficial results. In one embodiment, the silver particles are about 5 nm to 10 nm, about 10 nm to 20 nm, about 5 μm to 10 μm or about 10 μm to 20 μm average diameter.

For example, the composition/active agent(s) can be administered in dosages of at least about 0.0001 μg/kg to about 1 μg/kg, of at least about 0.01 μg/kg to about 5.0 μg/kg, at least about 0.1 μg/kg to about 2.5 μg/kg or at least about 1 μg/kg to about 5 μg/kg of body weight, although other dosages may provide beneficial results. In one embodiment, the silver particles are about 5 nm to 10 nm, about 10 nm to 20 nm, about 5 μm to 10 μm or about 10 μm to 20 μm average diameter.

For example, the composition/active agent(s) can be administered in dosages of at least about 0.0001 ng/kg to about 1 ng/kg, of at least about 0.01 ng/kg to about 5.0 ng/kg, at least about 0.1 ng/kg to about 2.5 μg/kg or at least about 1 μg/kg to about 5 μg/kg of body weight, although other dosages may provide beneficial results. In one embodiment, the silver particles are about 5 nm to 10 nm, about 10 nm to 20 nm, about 5 μm to 10 μm or about 10 μm to 20 μm average diameter.

Pharmaceutical formulations can be prepared by procedures known in the art using well known and readily available ingredients. For example, the silver particles can be formulated with one or more common excipients, diluents, or carriers, dyes, e.g., a fluorescent dye, a vital dye or a contrast dye.

The pharmaceutical formulations can also take the form of an aqueous or anhydrous solution, e.g., a lyophilized formulation, or dispersion, or alternatively the form of an emulsion or suspension.

In one embodiment, the compositions may be formulated for administration, e.g., by injection, for example, using a needle or a catheter, and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint.

Local delivery can be by a variety of techniques, e.g., using a catheter or needle. Examples of site-specific or targeted local delivery techniques are not intended to be limiting but to be illustrative of the techniques available. Examples include local delivery catheters, a needle, shunts or other devices.

The formulations and compositions described herein may also contain other ingredients such as antimicrobial agents or preservatives.

Some examples of other materials that may be formulated with the silver particles include but are not limited to agar acrylic polymers, polyacrylic acid, poly acryl methacrylate, gelatin, poly(lactic acid), pectin(poly glycolic acid), cellulose derivatives, cellulose acetate phthalate, nitrate, ethyl cellulose, hydroxyl ethyl cellulose, hydroxypropylcellulose, hydroxyl propyl methyl cellulose, hydroxypropylmethylcellulose phthalate, methyl cellulose, sodium carboxymethylcellulose, poly(ortho esters), polyurethanes, poly(ethylene glycol), poly(ethylene vinyl acetate), polydimethylsiloxane, poly(vinyl acetate phthalate), polyvinyl alcohol, polyvinyl 18liver18done, and shellac. Soluble starch and its derivatives for particle preparation include amylodextrin, amylopectin and carboxy methyl starch.

The silver particles may be formulated in hydrogels. Hydrogels can be classified as those with chemically cross-linked networks having permanent junctions or those with physical networks having transient junctions arising from polymer chain entanglements or physical interactions, e.g., ionic interactions, hydrogen bonds or hydrophobic interactions. Natural materials useful in hydrogels include natural polymers, which are biocompatible, biodegradable, support cellular activities, and include proteins like fibrin, collagen and gelatin, and polysaccharides like starch, alginate and agarose.

In one embodiment, silver nanoparticles may be administered by infusion or injection. Solutions of the compound (s) or its salts, can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion may include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In some cases, inclusion of isotonic agents, for example, sugars, buffers or sodium chloride is envisioned. Prolonged absorption of the injectable compositions can be brought about by the use in the compositions of agents delaying absorption, for example, microparticles, or aluminum monostearate and gelatin.

Sterile injectable solutions are prepared by incorporating the active agent in the required amount in the appropriate solvent with various of the other ingredients enumerated above, as required, followed by filter sterilization. In the case of sterile powders for the preparation of sterile injectable solutions, the methods of preparation include vacuum drying and the freeze drying techniques, which yield a powder of the active ingredient plus any additional desired ingredient present in the previously sterile-filtered solutions.

Useful solid carriers may include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as antimicrobial agents can be added to optimize the properties for a given use. Thickeners such as synthetic polymers, fatty acids, fatty acid salts and esters, fatty alcohols, modified celluloses or modified mineral materials can also be employed with liquid carriers Useful dosages of the compound(s) can be determined by comparing their in vitro activity and in vivo activity in animal models thereof. Methods for the extrapolation of effective dosages in mice, and other animals, to humans are known to the art; for example, see U.S. Pat. No. 4,938,949.

In one embodiment, the concentration of the silver particles in a liquid composition, may be from about 0.1-25 wt-%, e.g., from about 0.5-10 wt-%. The concentration in a semi-solid or solid composition such as a gel or a powder may be about 0.1-5 wt-%, e.g., about 0.5-2.5 wt-%.

Various embodiments use silver particles that have a diameter within a range of: 1 nm to 1000 nm; 1 nm to 500 nm; 1 nm to 300 nm; 1 nm to 100 nm, 1 nm to 75 nm, 1 nm to 40 nm, 5 nm to 1000 nm; 5 nm to 500 nm; 5 nm to 300 nm; 5 nm to 100 nm, 5 nm to 75 nm, 5 nm to 40 nm; 10 nm to 1000 nm; 10 nm to 500 nm; 10 nm to 300 nm; 10 nm to 100 nm, 10 nm to 75 nm, 10 nm to 40 nm; 50 nm to 1000 nm; 50 nm to 500 nm; 50 nm to 300 nm; or 50 nm to 100 nm. In one embodiment, the silver particles have a diameter within a range of: 100 nm to 500 nm; 100 μm to 300 nm; 50 nm to 100 nm, 25 nm to 75 nm, 10 nm to 40 nm, 50 nm to 500 nm; 50 nm to 200 nm; 5 nm to 30 nm; 5 nm to 10 nm, 5 nm to 50 nm, 5 nm to 40 nm; 10 nm to 100 nm; 10 nm to 50 nm; 10 nm to 30 nm; 1 nm to 10 nm, 1 nm to 7 nm, 1 nm to 5 nm; 5 nm to 20 nm; 5 nm to 15 nm; 2 nm to 8 nm; or 2 nm to 7 nm. Various embodiments use silver particles that have a diameter within a range of: 1 μm to 1000 μm; 1 μm to 500 μm; 1 μm to 300 μm; 1 μm to 100 μm, 1 μm to 75 μm, 1 μm to 40 μm, 5 μm to 1000 μm; 5 μm to 500 μm; 5 μm to 300 μm; 5 μm to 100 μm, 5 μm to 75 μm, 5 μm to 40 μm; 10 μm to 1000 μm; 10 μm to 500 μm; 10 μm to 300 μm; 10 μm to 100 μm, 10 μm to 75 μm, 10 μm to 40 μm; 50 μm to 1000 μm; 50 μm to 500 μm; 50 μm to 300 μm; or 50 μm to 100 μm. In one embodiment, the silver particles have a diameter within a range of: 100 μm to 500 μm; 100 μm to 300 μm; 50 μm to 100 μm, 25 μm to 75 μm, 10 μm to 40 μm, 50 μm to 500 μm; 50 μm to 200 μm; 5 μm to 30 μm; 5 μm to 10 μm, 5 μm to 50 μm, 5 μm to 40 μm; 10 μm to 100 μm; 10 μm to 50 μm; 10 μm to 30 μm; 1 μm to 10 μm, 1 μm to 7 μm, 1 μm to 5 μm; 5 μm to 20 μm; 5 μm to 15 μm; 2 μm to 8 μm; or 2 μm to 7 μm.

The term silver particles is intended to encompass any one or any combination of these size ranges. For example, some embodiments provide both a smaller range of particles, such as but not limited to nanoparticles, and a larger range of particles, such as but not limited to microparticles. Silver is radiopaque, but it is believed that the larger particles may be more visible to the X-ray-guided medical imaging, allowing the distributed particles to be better viewed by the clinician using the medical imaging. Various embodiments provide a combination of silver particle ranges, where a larger range is less than 50 wt-% of total weight of the silver particles. For example, the larger range may be less than 30 wt-%, less than 20 wt-%, less than 10 wt-% or less than 5 wt-% of the total weight of the silver particles.

Figure 5:
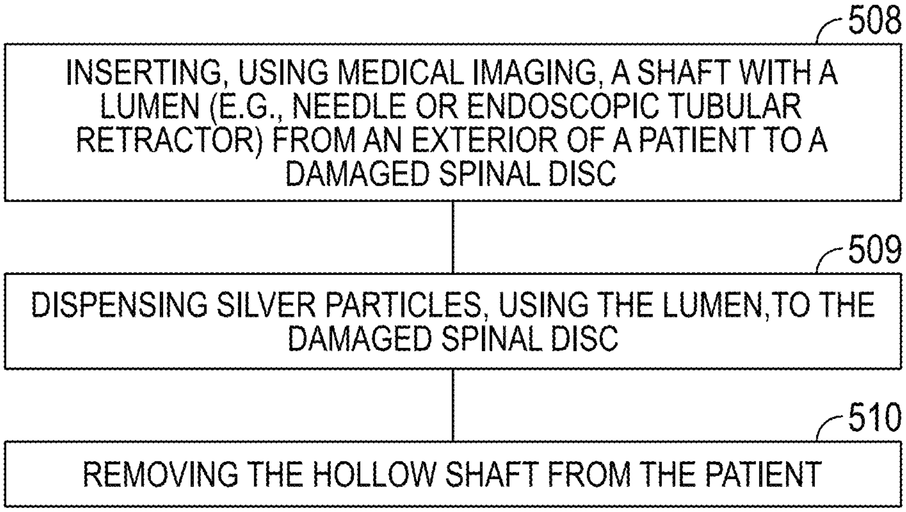
FIG. 5 illustrates, by way of example and not limitation, a method for treating a spinal disc using silver particles (e.g., nanoparticles and/or microparticles), such as to repair spinal disc injury or treat spinal disc disease.

FIG. 5 illustrates, by way of example and not limitation, a method for treating a spinal disc using silver particles (e.g., nanoparticles and/or microparticles), such as to repair spinal disc injury or treat spinal disc disease. The illustrated method includes inserting, using medical imaging, a shaft with a lumen extending from an exterior of a patient to the annular tear of the spinal disc 508. The silver nanoparticles or microparticles may be dispensed, using the lumen, to the annular tear of the spinal disc, as illustrated at 509. The hollow shaft may be removed the patient 510. Thus, various embodiments of the present subject matter provide a minimally-invasive technique to apply silicon nanoparticles or microparticles to repair the annular tear. Blood loss for the procedure is minimal (e.g., a few drops). By way of example, the hollow shaft may have a diameter within a range from 1 mm to 12 mm. In some embodiments, the shaft has a diameter between 1 mm to 10 mm, or between 1 mm to 6 mm. By way of example and not limitation, a 4 mm diameter tube may be used to perform an endoscopic procedure at the annular tear. Medical imaging may be used for localizing the damaged disc, and navigating to the damaged disc. Localizing involves identifying the disc that is damaged, and navigating involves planning the path to access the damaged disc which may involve avoiding blood vessels, nerves and organs such as lungs. The use of medical imaging to access the damaged disc may include at least one of using X-ray guided imaging to access the damaged disc, using stereotactic techniques to access the damaged disc, or using robotic navigation to access the disc. X-ray guided imaging include CT scans or fluoroscopy. Robotic navigation or robotic guidance may use X-ray imaging or frameless navigation. By way of example and not limitation, Medtronic's StealthStation™ surgical navigation system may be used in the procedure to access the damaged disc.

According to some embodiments, the silver particles are dispensed through a needle, such as a hypodermic needle. A specific example of a needle is an introducer needle such as a guidewire introducer needle. According to some embodiments, the shaft is an endoscopic tubular retractor (or tubular retractor) extending from an exterior of the patient to the annular tear in the injured spinal disc. The silver nanoparticles may be dispensed using the endoscopic tubular retractor, either with or without the use of endoscopic tool(s) inserted into the endoscopic tubular retractor. For example, the silver particles may be dispensed into the endoscopic tubular retractor, and the tube may be manipulated to direct the silver particles to the surfaces of the annular tear. The sliver particles may be gravity fed and poured out of the end of the endoscopic tubular retractor.

By way of example and not limitation, the tool may include a syringe with a barrel containing the silver particles, a plunger, and a needle advanced into the lumen of the endoscopic tubular retractor to dispense the silver particles to the annular tear by actuating the plunger to push the silver particles through the needle. The needle may be a hypodermic needle or a flexible dispensing needle. The tool may include a steerable catheter configured to dispense the silver particles to the annular tear, where a distal end of the steerable catheter may be fed through the lumen of the endoscopic tubular retractor and steered to dispense the silver particles through a lumen in the steerable catheter to the annular tear. The silver particles may be introduced into the lumen in the steerable catheter, using gravity to dispense the silver particles to the annular tear. The tool may include an endoscopic camera to visualize a distribution of the silver particles on a surface of the spinal disc in or near the annular tear. The camera may be used to confirm whether the distribution of silver particles is appropriate or needs to be adjusted (e.g., added, moved or removed). The tool may be configured to atomize the silver particles into an aerosol or small droplets into a gas phase to coat a torn surface of an annulus fibrosis of the spinal disc. In some embodiments, sterile compressed air, which is appropriate for introduction into a surgical field, may be used to atomize the silver particles to coat the torn surface. In some embodiments, air in a syringe may be used to atomize the silver particles to coat the torn surface of the annulus fibrosis of the spinal disc.

Figure 6:
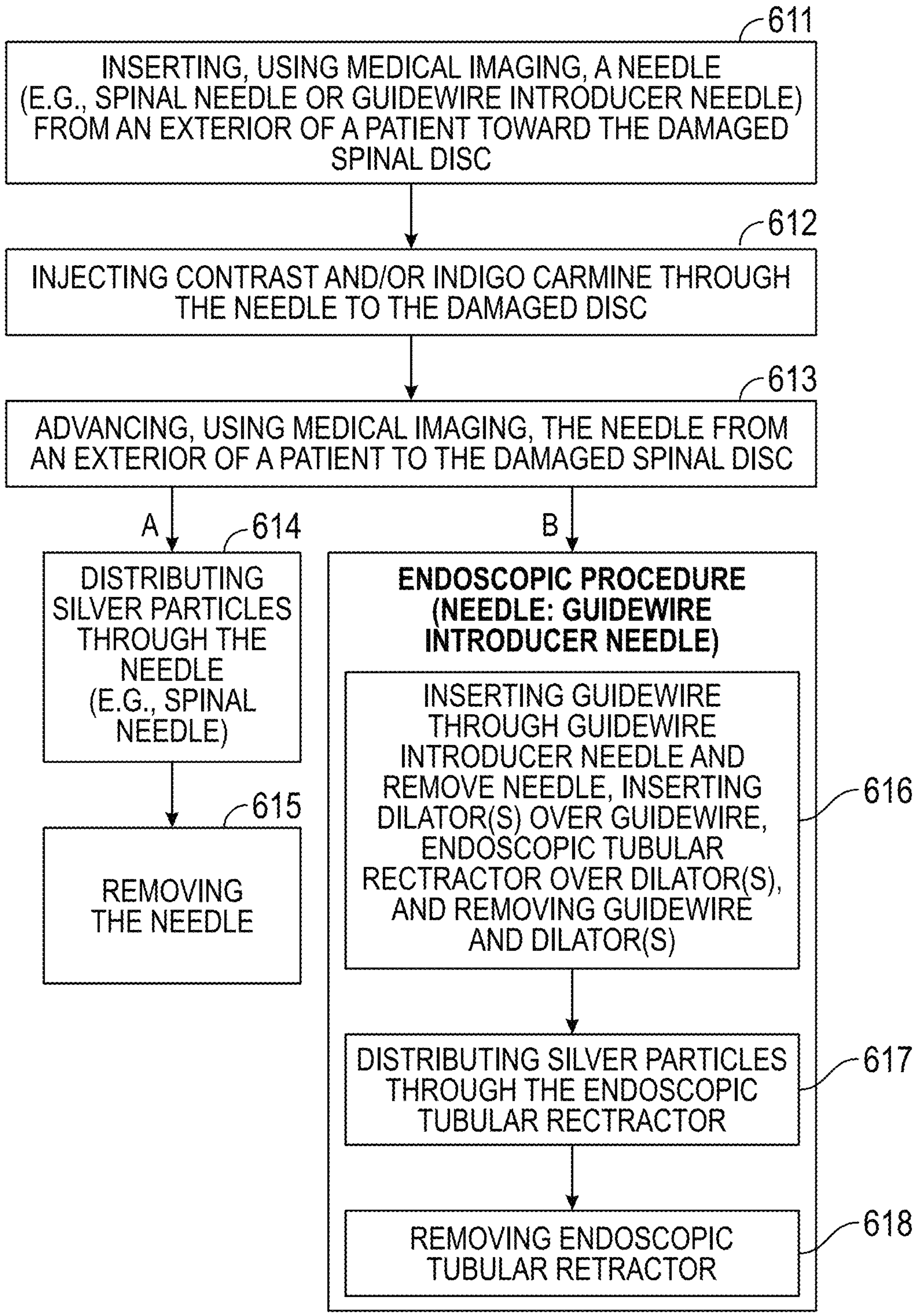
FIG. 6 illustrates, by way of example and not limitation, methods for treating a spinal disc such as to repair spinal disc injury or treat spinal disc disease, including a method in which the silver particles (e.g., nanoparticles and/or microparticles) are introduced through a needle and a method in which the silver particles are introduced through an endoscopic tubular extractor.

FIG. 6 illustrates, by way of example and not limitation, methods for treating a spinal disc such as to repair spinal disc injury or treat spinal disc disease, including a method in which the silver particles (e.g., nanoparticles and/or microparticles) are introduced through a needle and a method in which the silver particles are introduced through an endoscopic tubular extractor. endoscopic tubular retractor. The method may include inserting, using a medical imaging, a needle from an exterior of a patient toward the injured spinal disc, as illustrated at 611. At 612, a dye may be injected into the patient to assist with identifying the injured tissue. The dye may include a contrast dye for use with x-ray imaging technology. Additionally or alternatively, the dye may include a component such as indigo carmine that stains the acidic nucleus pulposus and enhances the visualization of the tissue using an endoscope. Medical imaging, as enhanced by the contrast dye, may continue to be used to advance the needle to the annular tear in injured spinal disc 613. FIG. 6 further illustrates two methods (A or B) that may be used once the needle is positioned. The first method (A) includes distributing silver particles through the needle to the annular tear 614, after which the needle may be removed 615. The second method (B) includes performing an endoscopic procedure. The needle may be a guidewire introducer needle. The second method may include inserting the guidewire through the guidewire introducer needle and advancing the guidewire to the injured disc and removing the guidewire introducer needle, and inserting one or more dilator(s) over the guidewire and advancing the dilator(s) to the injured spinal disc, as illustrated at 616. It is noted that one dilator may be used, or a series of dilators of increasing size may be used to prepare the tissue to have the endoscopic tubular retractor inserted. The second method may further include inserting an endoscopic tubular retractor (e.g., tubular extractor) over the dilator(s) and advancing the endoscopic tubular retractor to the injured spinal disc. The guidewire and dilator(s) may be removed, leaving the endoscopic tubular retractor extending from the exterior of the patient to the injured tissue. The endoscopic procedure may include debriding the annular tear and the herniation. At 617, the second method may include distributing the silver particles through the endoscopic tubular retractor to the annular tear. An endoscope may be used to visualize the silver particles after being distributed through the endoscopic tubular retractor to confirm that the distribution of silver particles on the annular tear is sufficient. A color additive (e.g., dye) may be included with the distributed silver particles to enhance visualization using the endoscope. The composition of the silver nanoparticles may enable visualization using X-ray guided technology or other medical imaging. The endoscopic tubular retractor may be removed after the particles have been distributed 618.

Figure 7:
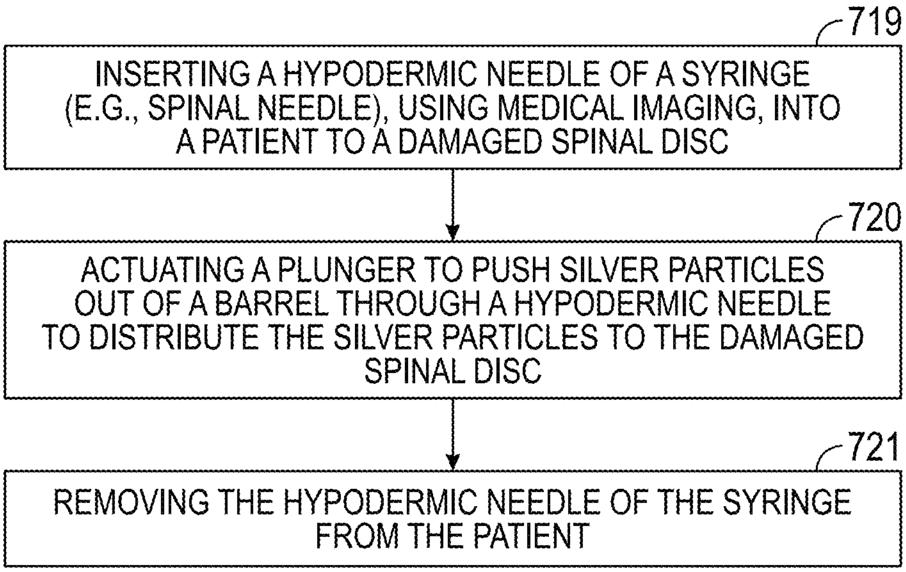
FIG. 7 illustrates, by way of example and not limitation, a method in which the silver particles (e.g., nanoparticles and/or microparticles) are introduced through a needle.

FIG. 7 illustrates, by way of example and not limitation, a method in which the silver particles (e.g., nanoparticles and/or microparticles) are introduced through a needle. The illustrated method includes inserting the hypodermic needle of the syringe, using medical imaging, into the patient to the annular tear of the spinal disc 719, actuating the plunger to push the silver particles out of the barrel through the hypodermic needle to distribute the silver particles to the annular tear of the spinal disc 720; and removing the hypodermic needle of the syringe from the patient 721.

Figure 8:
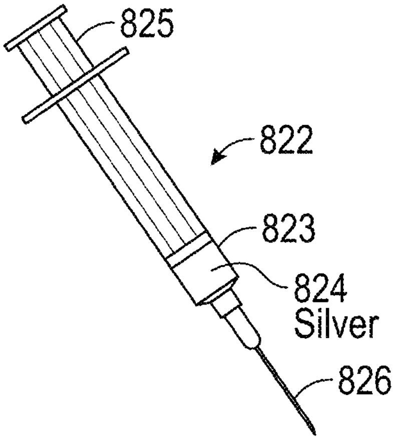
FIG. 8 illustrates, by way of example and not limitation, a kit, including a syringe prefilled with silver particles (e.g., nanoparticles and/or microparticles), used to administer silver particles to a damaged spinal disc.

FIG. 8 illustrates, by way of example and not limitation, a kit, including a syringe prefilled with silver particles (e.g., nanoparticles and/or microparticles), used to administer silver particles to a damaged spinal disc. The syringe 822 includes a barrel 823 with the silver particles 824 therein, a plunger 825 and a needle 826. The syringe is configured to distribute the silver particles through the needle when the plunger is pushed into the barrel. The illustrated system may be a kit, in which the syringed is pre-filled with the silver particles before distribution to the user. The needle may include a spinal needle or other needle configured to reach tissue near a spine. The silver particles may be a dry powder, may be in a liquid solution, may be in a gel suspension, or may take any form discussed in this document. Liquid solution examples may include silver particles and saline or may include silver particles and a Lactated Ringer's solution. The silver nanoparticles may be within a range between 1 nm and 1000 nm. The silver particles may have a hydroxyethyl cellulose coating, which has been studied and proven to have a very low toxicity to the human cells.

Figure 9:
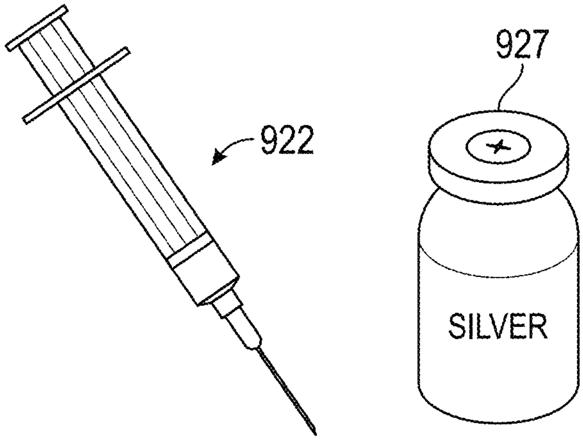
FIG. 9 illustrates, by way of example and not limitation, a kit including a syringe and a separate container of silver particles (e.g., nanoparticles and/or microparticles) for use in administering silver particles to an annular tear.

FIG. 9 illustrates, by way of example and not limitation, a kit including a syringe and a separate container of silver particles (e.g., nanoparticles and/or microparticles) for use in administering silver particles to a damaged spinal disc. The container of silver particles 927 may be distributed alone or in conjunction with the needle (e.g., syringe 922) used to access the injured spinal disc. The silver particles may be a dry powder, may be in a liquid solution, may be in a gel suspension, or may take any form discussed in this document. Liquid solution examples may include silver particles and saline or may include silver particles and a Lactated Ringer's solution. The silver nanoparticles may be within a range between 1 nm and 1000 nm. The silver nanoparticles may have a hydroxyethyl cellulose coating.

Figure 10:
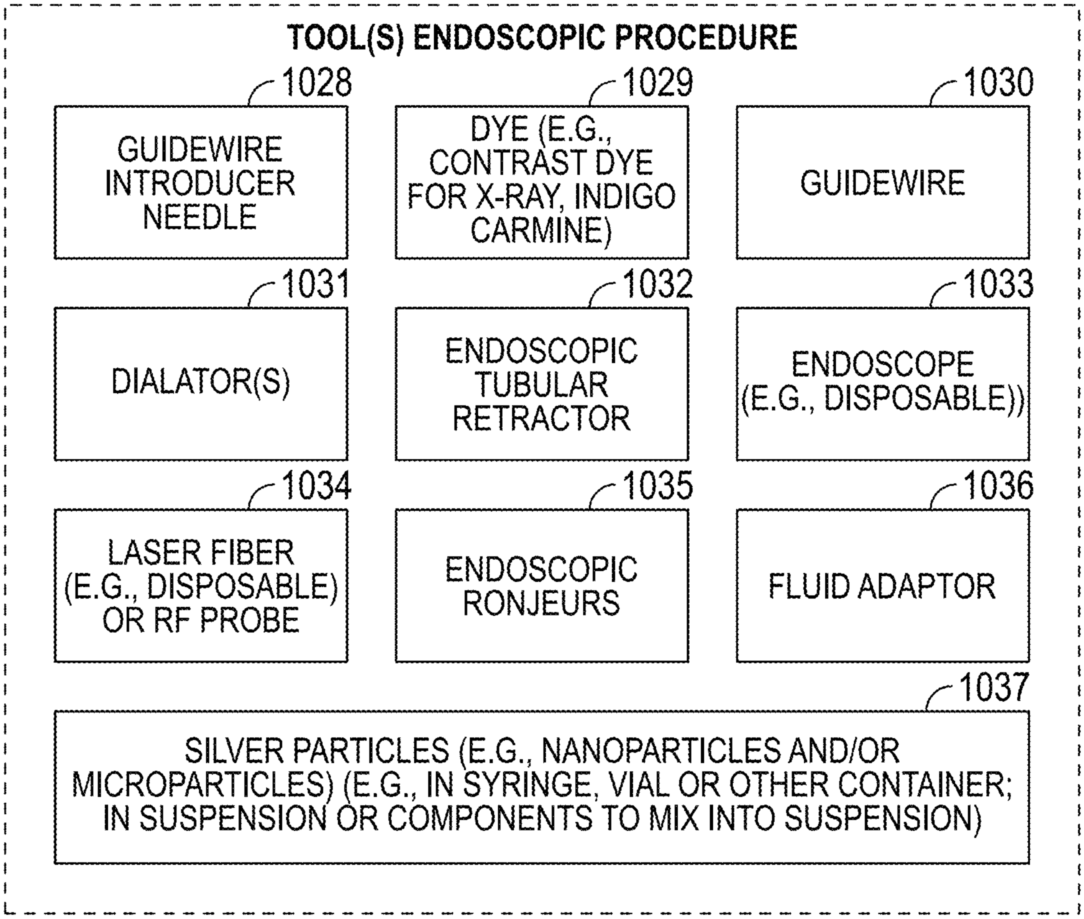
FIG. 10 illustrates, by way of example and not limitation, various tools that may be used to perform an endoscopic procedure, where one or more of the tools may be included in a kit for use in administering silver particles (e.g., nanoparticles and/or microparticles) to a damaged disc, such as to repair spinal disc injury or treat spinal disc disease.

FIG. 10 illustrates, by way of example and not limitation, various tools that may be used to perform an endoscopic procedure, where one or more of the tools may be included in a kit for use in administering silver particles (e.g., nanoparticles and/or microparticles) to a damaged disc, such as to repair spinal disc injury or treat spinal disc disease. The kit, with one or more of the illustrated tools, may be distributed to the user for use to perform the endoscopic procedure. Examples of tool(s) that may be in the kit include a guidewire introducer needle 1028, dye (contrast dye for X-ray and/or indigo carmine) 1029, a guidewire 1030, a dilator or a system of dilators of different sizes 1031, an endoscopic tubular retractor 1032, an endoscope such as a disposable endoscope 1033, a laser fiber or RF probe such as a disposable laser fiber or RF probe 1034, an endoscopic rongeurs 1035, a fluid adaptor 1036 to be attached to the end of the endoscopic tubular retractor for creating a vacuum and sucking out fluid (including irrigation) and debris and/or silver particles 1037 in any form discussed herein in this document. The dye may be premixed with the contrast dye and indigo carmine, or the dye may be distributed with the contrast dye and indigo carmine separated, and the clinical team may combine before performing the endoscopic procedure.

Figure 11:
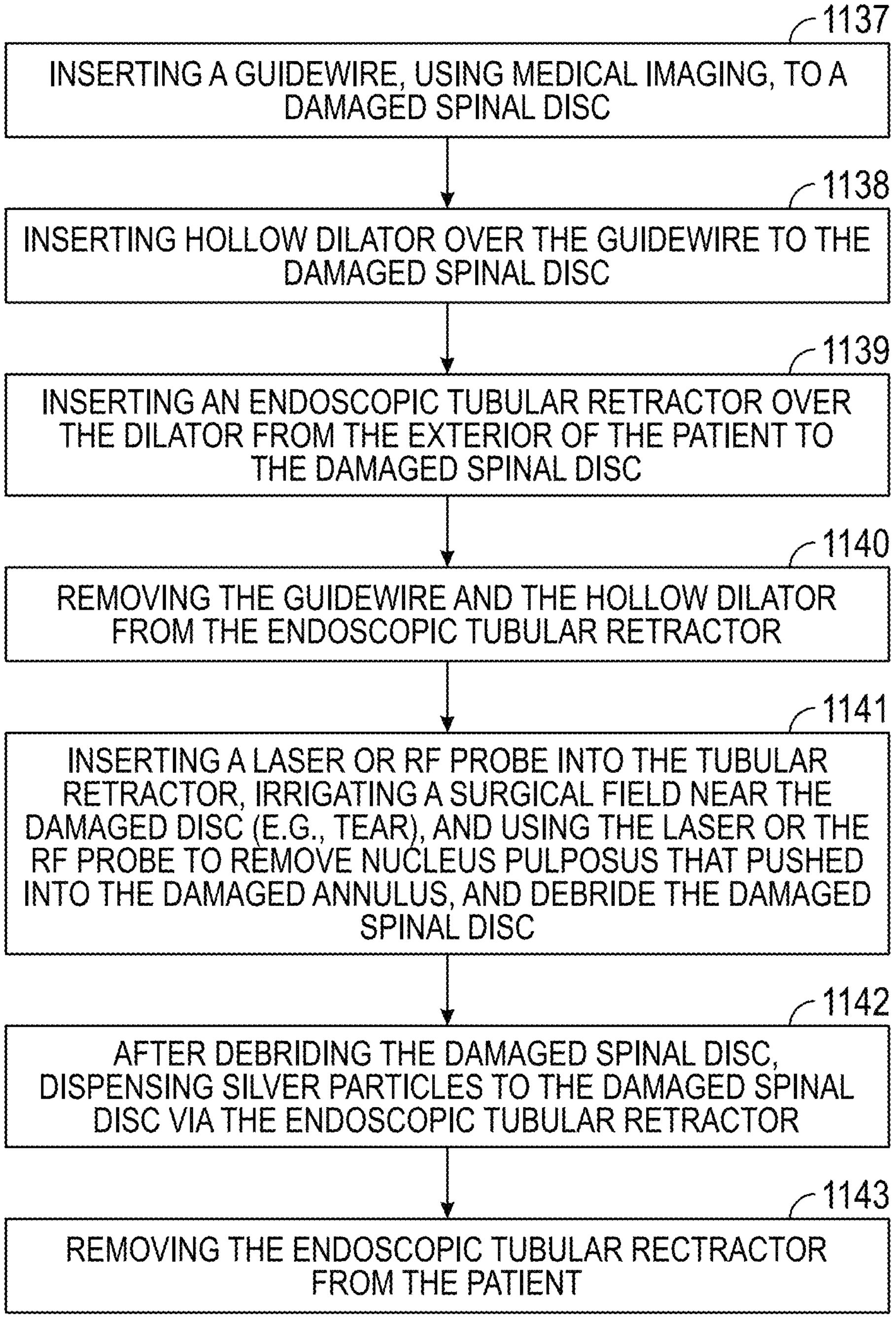
FIG. 11 illustrates, by way of example and not limitation, a method for endoscopically debriding the damaged disc and then administering the silver particles (e.g., nanoparticles and/or microparticles) to the damaged disc.

FIG. 11 illustrates, by way of example and not limitation, a method for endoscopically debriding the damaged disc and then administering the silver particles (e.g., nanoparticles and/or microparticles) to the damaged disc. The illustrated method for treating an annular tear of a spinal disc of a patient may include inserting a guidewire 1137, using medical imaging, from an exterior of the patient to the annular tear of the spinal disc, inserting a hollow dilator over the guidewire to the annular tear of the spinal disc 1138, inserting an endoscopic tubular retractor over the dilator from the exterior of the patient to the annular tear 1139, removing the guidewire and the hollow dilator from the endoscopic tubular retractor 1140, inserting a laser or radio frequency (RF) probe into the endoscopic tubular retractor, irrigating a surgical field near the annular tear, and using the laser or the RF probe to remove nucleus pulposus that pushed through the annular tear and debride the annular tear of the spinal disc 1141, dispensing silver particles to the annular tear of the spinal disc via the endoscopic tubular retractor after debriding the annular tear 1142, and removing the endoscopic tubular retractor from the patient 1143.

Figure 12:
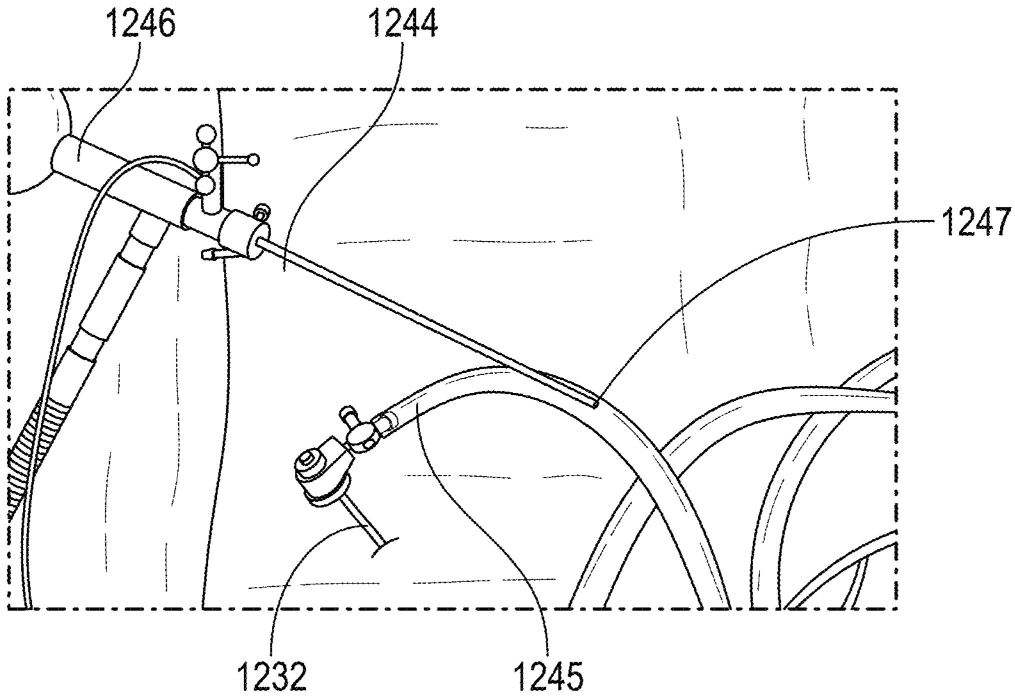
FIG. 12 illustrates, by way of example and not limitation, an endoscopic tubular extractor, an endoscopic tool with irrigation, a camera, and laser fiber used during a surgical procedure to debride a damaged disc.

FIG. 12 illustrates, by way of example and not limitation, an endoscopic tubular extractor 1232, an endoscopic tool 1244 with irrigation 1245, a camera 1246, and laser fiber 1247 used during a surgical procedure to debride a damaged disc. All surgical activities involving the annular tear may be performed through the tubular extractor. The laser fiber may be used to debride the inflamed tissue from the annular tear.

Figure 13:
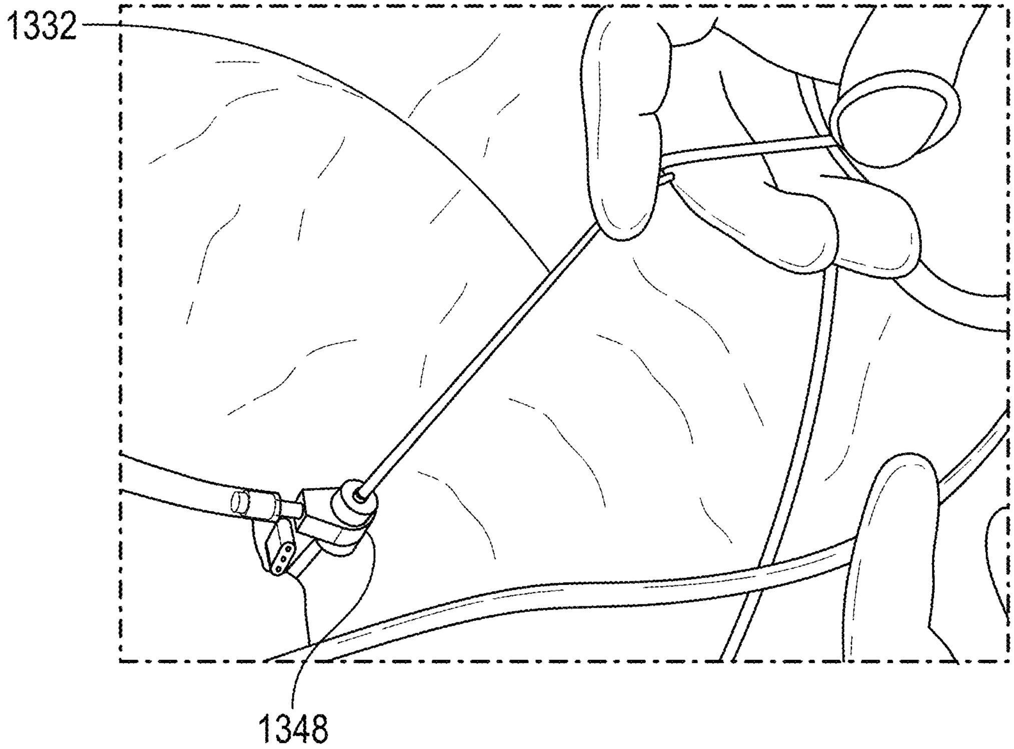
FIG. 13 illustrates, by way of example and not limitation, an endoscopic tubular extractor and a rongeurs inserted into the tubular extractor, wherein the rongeurs may be used to remove pieces of inflammation from the surgical field around the damaged disc (e.g., annular tear) or may be used to distribute the silver particles (e.g., nanoparticles and/or microparticles) to the annular tear.

FIG. 13 illustrates, by way of example and not limitation, an endoscopic tubular extractor 1332 and a rongeurs 1348 inserted into the tubular extractor. The rongeurs may be used to remove pieces of inflammation from the surgical field around the damaged disc (e.g., annular tear) or may be used to distribute the silver particles (e.g., nanoparticles and/or microparticles) to the damaged disc. For example, some silver particles may be gripped using the rongeurs, inserted through the tubular extractor, and released into contact with the annular tear.

Figure 14:
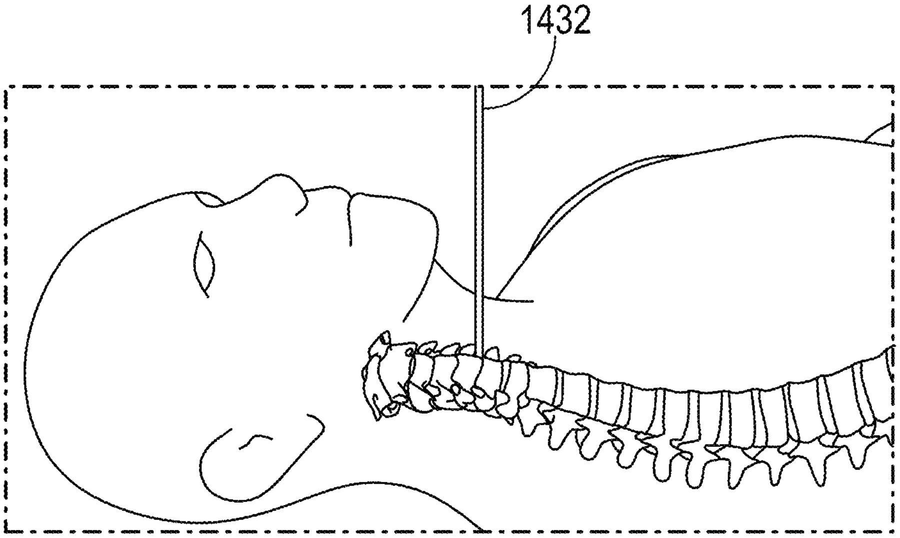
FIG. 14 illustrates, by way of example and not limitation, an endoscopic procedure, including an endoscopic tubular extractor inserted into a patient's neck to access a cervical disc.
Figure 15:
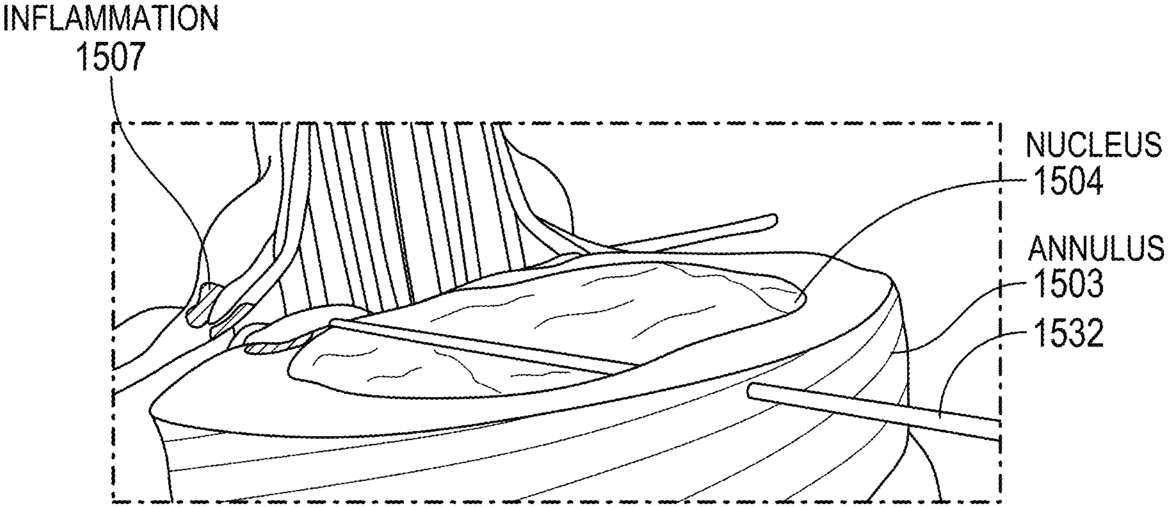
FIG. 15 illustrates, by way of example and not limitation, the endoscopic tubular extractor extending through the spinal disc to access a damaged region (e.g., annular tear) of the spinal disc.
Figure 16:
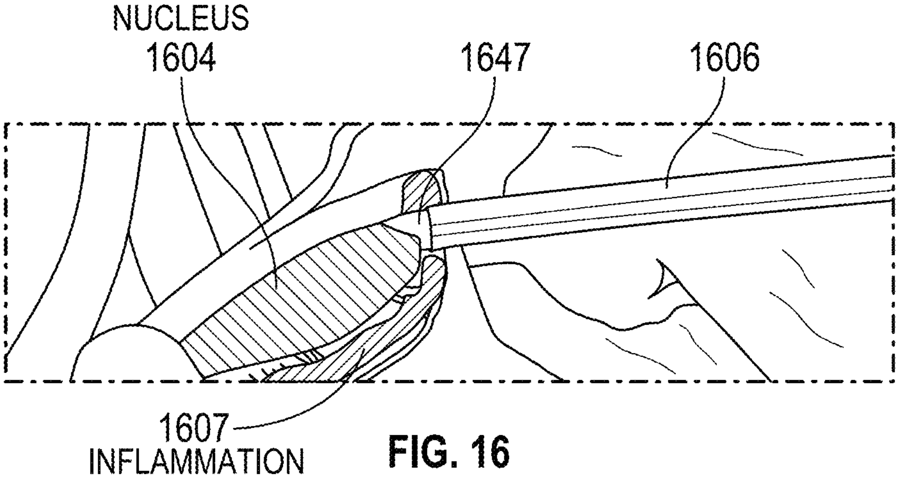
FIG. 16 illustrates, by way of example and not limitation, a laser debriding the damaged spinal disc.

FIG. 14 illustrates, by way of example and not limitation, an endoscopic procedure, including an endoscopic tubular extractor inserted into a patient's neck to access a cervical disc. A very small incision is made to receive the tubular retractor 1432. The surgical path for the needle, guidewire, dilator(s) and the tubular retractor 1532 is directed from the front of the neck to the front (anterior side) of the spinal disc through the anulus 1503 and nucleus 1504 to the damaged disc (e.g., annular tear) and inflamed tissue 1507 on the posterior side of the spinal disc, as generally illustrated in FIG. 15. FIG. 16 illustrates, by way of example and not limitation, a laser 1647 extending from the endoscopic tool 1606 and through the nucleus 1604 and debriding the damaged spinal disc. A surgeon may manipulate the tips of the laser and/or the tubular extractor to debride the tear. An endoscope/camera allows the surgeon to see and target the inflamed tissue 1607 with the laser.

Figure 17:
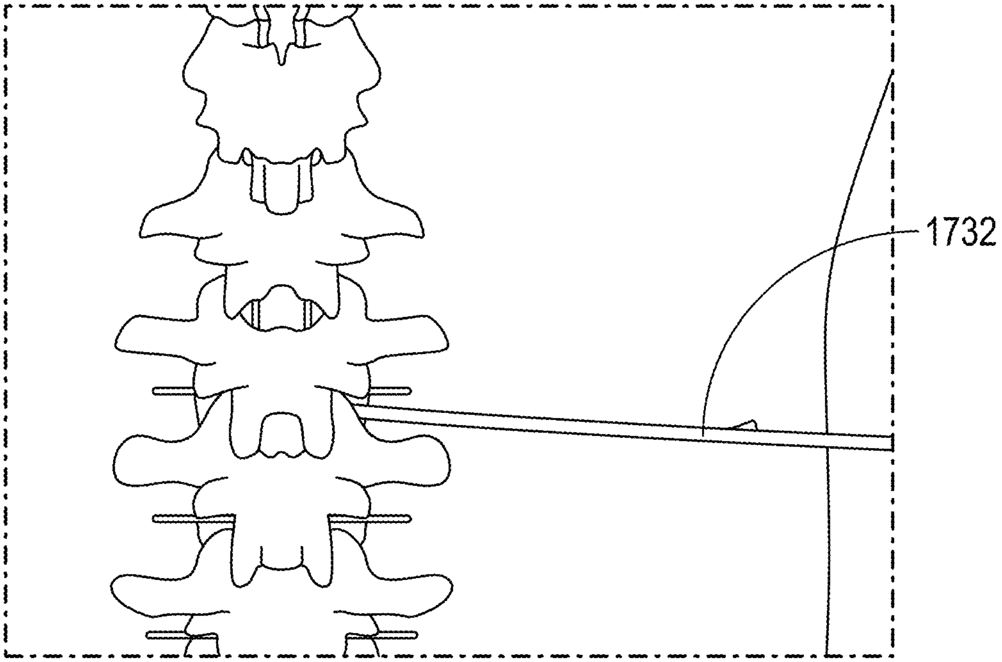
FIG. 17 illustrates, by way of example and not limitation, an endoscopic procedure, including an annular tubular extractor inserted into a patient's side to access a lumbar disc.

FIG. 17 illustrates, by way of example and not limitation, an endoscopic procedure, including an endoscopic tubular extractor inserted into a patient's side to access a lumbar annular tear. A very small incision is made to receive the tubular retractor 1732. The surgical path for the needle, guidewire, dilator(s) and the tubular extractor is directed from the patient's side through a foramen to the posterior side of the spinal disc near the annular tear.

Figure 18:
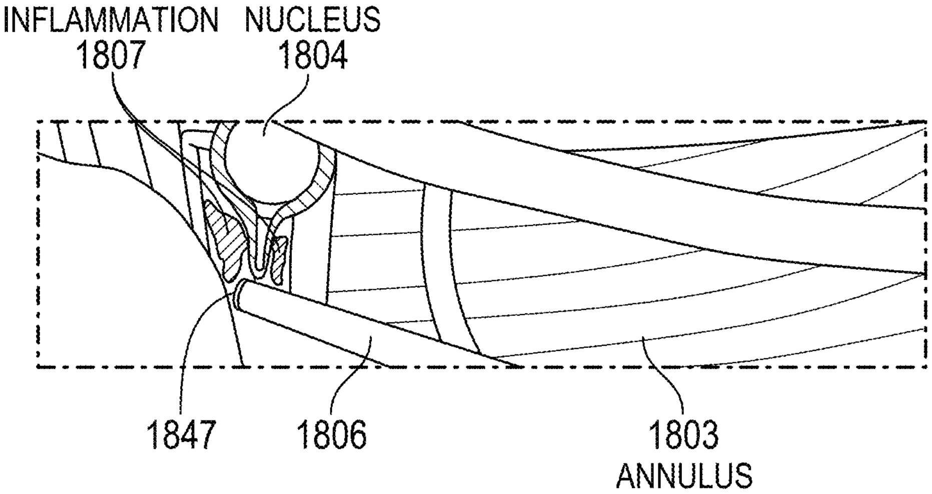
FIG. 18 illustrates, by way of example and not limitation, a laser debriding the damaged spinal disc. after accessing the tear from the posterior side of the spinal disc

FIG. 18 illustrates, by way of example and not limitation, a laser 1847 extending from the endoscopic tool 1806 debriding the inflamed tissue 1807 of the damaged disc (e.g., annular tear) located at a periphery of the nucleus 1804 after accessing the tear from the posterior side of the spinal disc. A surgeon may manipulate the tips of the laser and/or the endoscopic tubular extractor to debride the annulus 180, including removing nucleus in the tear. An endoscope/camera allows the surgeon to see and target the inflamed tissue with the laser.

Figure 19:
FIG. 19 illustrates a view of an introducer needle advanced toward the injured spinal disc.
Figure 20:
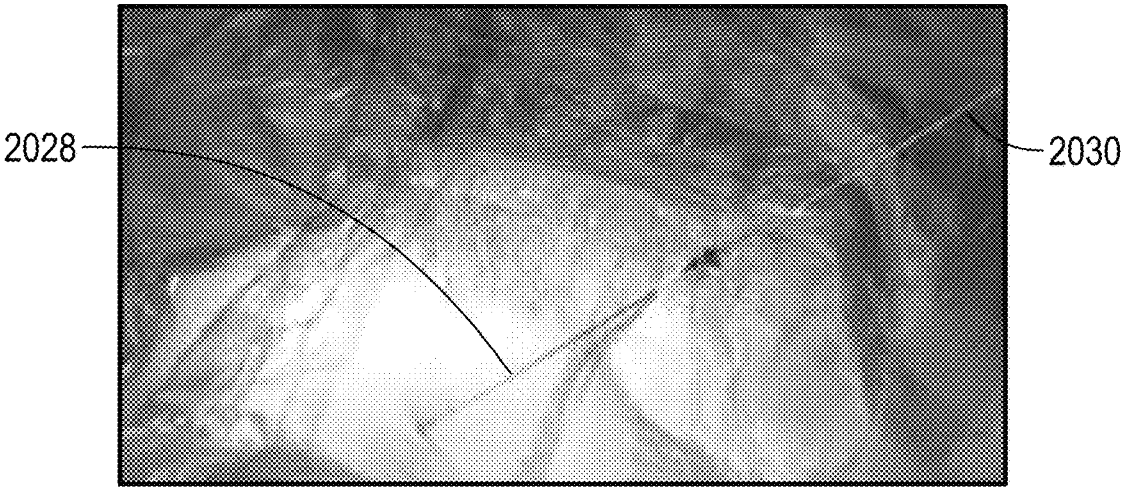
FIG. 20 illustrates a view of a guidewire inserted through the introducer for advancement to the injured disc under medical imaging.
Figure 21:
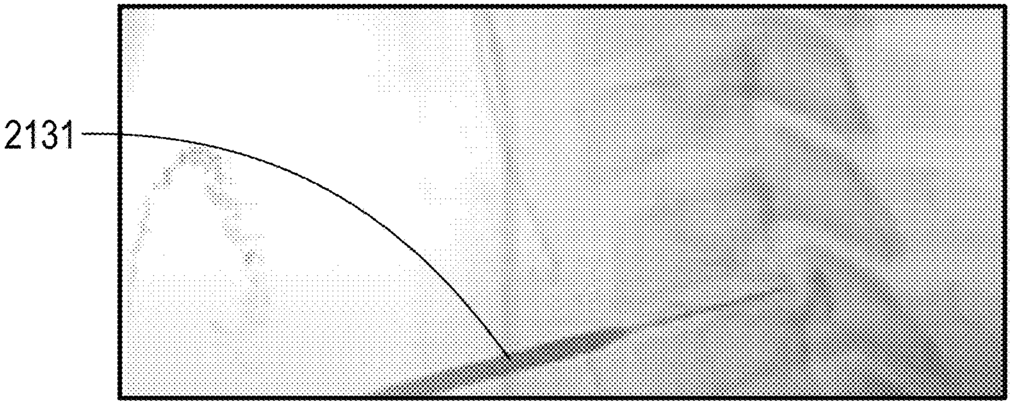
FIG. 21 illustrates a view of a dilater inserted over the guidewire and advanced toward the damaged spinal disc
Figure 22:
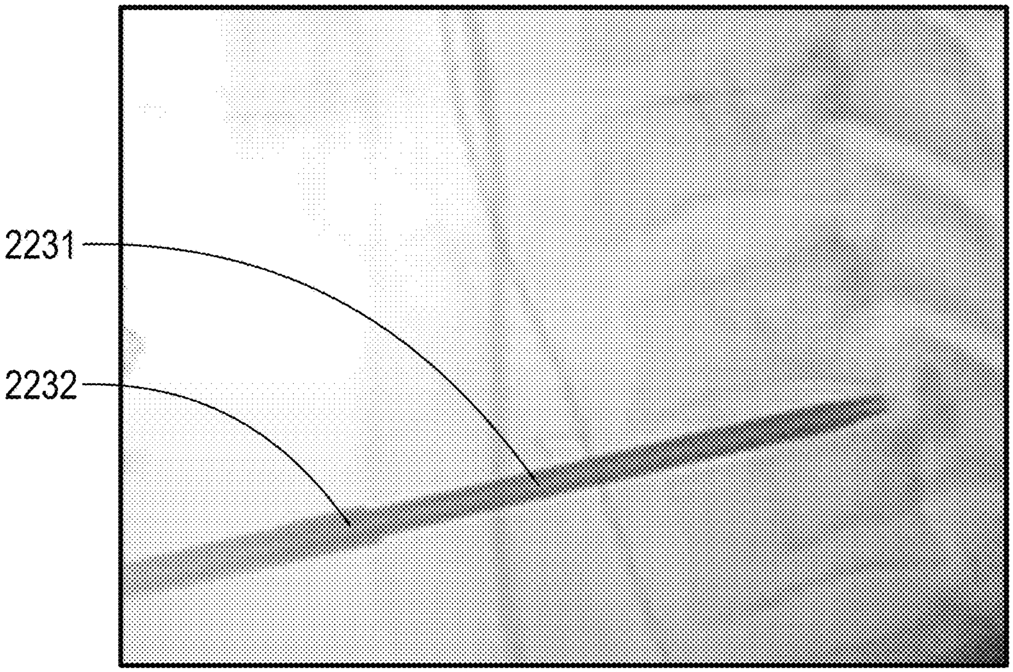
FIG. 22 illustrates a view of a tubular extractor, or endoscopic tubular retractor, inserted over the dilator and advanced toward the damaged disc.
Figure 23:
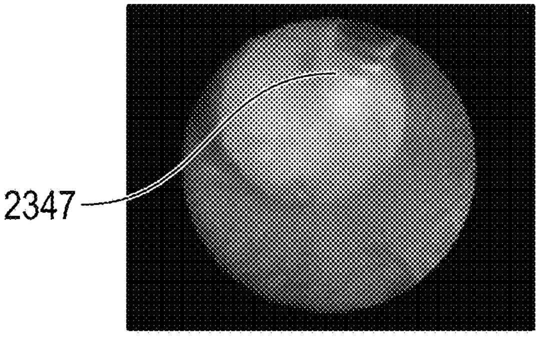
FIG. 23 illustrates an endoscopic camera view of a laser debriding inflammation from a damaged spinal disc.
Figure 24:
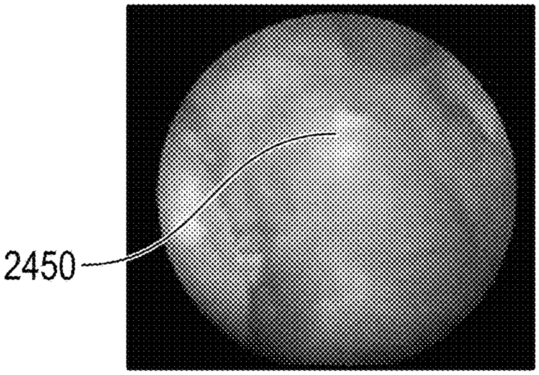
FIG. 24 illustrates an endoscopic camera view of an exposed nerve root after debriding the inflammation.

FIGS. 19-24 illustrate examples of medical imaging used to access the injured spinal disc in a minimally invasive manner. FIG. 19 illustrates a medical imaging view of an introducer needle 1928 advanced toward the damaged spinal disc. A dye (e.g., contrast and/or indigo carmine) may be injected. FIG. 20 illustrates a view of a guidewire 2030 inserted through the introducer 2028 for advancement to the damaged spinal disc under medical imaging. FIG. 21 illustrates a view of a dilater 2131 inserted over the guidewire and advanced toward the injured spinal disc. FIG. 22 illustrates a view of an endoscopic tubular extractor 2232 inserted over the dilator 2231 and advanced toward the damaged disc. After the tubular extractor is positioned, the guidewire and dilator may be removed. The surgeon can perform the procedure through the tubular extractor. FIG. 23 illustrates an endoscopic camera view of a laser 2347 debriding inflammation from a herniated disc, and FIG. 24 illustrates an endoscopic camera view of an exposed nerve root 2450 after debriding the inflamed tissue from the tear. It can be seen that the nerve root has been inflamed by the tissue. It is again noted that the endoscopic camera may be used to visualize the distribution of the silver particles (e.g,, nanoparticles and/or microparticles) after the tear has been debrided. The silver particles may be distributed with a color additive (e.g., fluorescent dye) that enhances visualization using the endoscopic camera.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using combinations or permutations of those elements shown or described.

The above description is intended to be illustrative, and not restrictive. For example, the above-described examples (or one or more aspects thereof) may be used in combination with each other. Other embodiments may be used, such as by one of ordinary skill in the art upon reviewing the above description. The scope of the invention should be determined with reference to the appended claims, along with the full scope of equivalents to which such claims are entitled.

What is claimed is:

1. A method for treating or repairing a damaged spinal disc of a patient, comprising:

inserting, using medical imaging, a hollow shaft with a lumen extending from an exterior of the patient to the damaged spinal disc;

surgically debriding an annular tear in the damaged spinal disc through the lumen of the hollow shaft to provide a treated annular tear;

providing a tool comprising a syringe with a barrel and a plunger, the barrel containing silver particles;

dispensing the silver particles from the barrel and through the lumen of the hollow shaft to an exterior surface of the treated annular tear by actuating the plunger; and removing the hollow shaft from the patient.

2. The method of claim 1, wherein the hollow shaft is within a range from 1 mm to 12 mm in diameter.

3. The method of claim 2, wherein the inserting the shaft includes inserting a hypodermic needle, using the medical imaging, to the damaged spinal disc.

4. The method of claim 2, wherein the shaft is an endoscopic tubular retractor, the method further including inserting a guidewire, using a guidewire introducer needle and the medical imaging, to the damaged spinal disc, inserting at least one hollow dilator over the guidewire to the damaged spinal disc, inserting the endoscopic tubular retractor over the at least one hollow dilator to the damaged spinal disc, and removing the guidewire and the at least one hollow dilator from the endoscopic tubular retractor, wherein the endoscopic tubular retractor includes the lumen used to dispense silver particles to the exterior surface of the treated annular tear.

5. The method of claim 4, further comprising inserting the tool into the endoscopic tubular retractor to dispense the silver particles to the exterior surface of the treated annular tear.

6. The method of claim 5, wherein the tool further comprises a steerable catheter, and the dispensing includes feeding a distal end of the steerable catheter through the lumen of the endoscopic tubular retractor and steering the distal end to dispense the silver particles through a lumen in the steerable catheter to the exterior surface of the treated annular tear.

7. The method of claim 1, wherein the syringe includes a needle, and the needle is advanced into a lumen of an endoscopic tubular retractor to dispense the silver particles to the exterior surface of the treated annular tear through the needle.

8. The method of claim 7, wherein the needle includes a hypodermic needle or a flexible dispensing needle.

9. The method of claim 1, further comprising using an endoscopic camera to visualize a distribution of the silver particles on the exterior surface of the treated annular tear.

10. The method of claim 1, further comprising atomizing the silver particles into an aerosol or small droplets into a gas phase to coat the exterior surface of the treated annular tear, wherein the silver particles are contained in the barrel in a dry powder form.

11. The method of claim 10, further comprising using sterile compressed air to atomize the silver particles to coat the exterior surface of the treated annular tear, wherein the sterile compressed air is appropriately sterile for introduction into a surgical field.

12. The method of claim 10, further comprising using air in the syringe to atomize the silver particles to coat the exterior surface of the treated annular tear.

13. The method of claim 1, wherein the inserting the shaft using medical imaging includes using at least one of X-ray guided imaging, stereotactic techniques, or robotic navigation to insert the shaft.

14. The method of claim 1, further comprising using the medical imaging to advance the hollow shaft through a foramen in a spine to access the damaged spinal disc.

15. The method of claim 1, further comprising advancing the hollow shaft to enter an anterior side of the damaged spinal disc to a damage on a posterior side of the damaged spinal disc.

16. The method of claim 1, wherein the silver particles have dimensions within a range between 1 nm and 1000 nm.

17. The method of claim 1, wherein the silver particles are coated with hydroxyethyl cellulose.

18. The method of claim 1, wherein surgically debriding an annular tear in the damaged spinal disc comprises using a laser.

19. The method of claim 1, wherein surgically debriding an annular tear in the damaged spinal disc comprises using a radio frequency probe.

20. The method of claim 1, wherein the silver particles are in a dry powder.

21. The method of claim 1, wherein the silver particles are in a liquid solution.

22. A method for treating a spinal disc of a patient, comprising: inserting, using medical imaging, a hollow shaft with a lumen extending from an exterior of the patient to the spinal disc; surgically debriding an annular tear in the spinal disc through the lumen of the hollow shaft; providing a tool comprising a syringe with a barrel and a plunger, the barrel containing silver particles in one of a dry powder or a liquid solution; actuating the plunger to dispense the silver particles from the barrel and through the lumen of the hollow shaft to the spinal disc without inserting the lumen into the spinal disc; and removing the hollow shaft from the patient.

* * * * *